United States Patent [19]
Blizzard et al.

[11] Patent Number: 5,114,930
[45] Date of Patent: May 19, 1992

[54] AVERMECTIN DERIVATIVES WITH A SPACER INSERTED BETWEEN THE DISACCHARIDE AND THE AGLYCONE USEFUL AS ANTIPARASITIC AGENTS

[75] Inventors: Timothy A. Blizzard, Rahway; Gaye Margiatto, Freehold, both of N.J.

[73] Assignee: Merck & Co., Inc., Rahway, N.J.

[21] Appl. No.: 522,709

[22] Filed: May 14, 1990

[51] Int. Cl.$^5$ .................... A61K 31/70; C07H 17/04
[52] U.S. Cl. ........................ 514/30; 536/7.1
[58] Field of Search .................. 514/30; 536/7.1

[56] References Cited

U.S. PATENT DOCUMENTS 4,587,247  5/1986  Linn et al. ............... 549/264

FOREIGN PATENT DOCUMENTS 2387231  12/1978  France ................ 536/7.1

*Primary Examiner*—Johnnie R. Brown
*Assistant Examiner*—Elli Peselev
*Attorney, Agent, or Firm*—Hesna J. Pfeiffer; David L. Rose

[57] ABSTRACT

There are disclosed avermectin derivatives which incorporate a spacer between the disaccharide and the aglycone. The synthetic spacer-containing analogs are derived from the corresponding aglycones which in turn are prepared by chemical modification of naturally occurring avermectins. The compounds are active antiparasitic agents and compositions for that use are disclosed.

23 Claims, No Drawings

AVERMECTIN DERIVATIVES WITH A SPACER INSERTED BETWEEN THE DISACCHARIDE AND THE AGLYCONE USEFUL AS ANTIPARASITIC AGENTS

BACKGROUND OF THE INVENTION

The avermectins (previously referred to as C-076 comopunds) are a series of compounds produced by fermentation of avermectin producing strains of *Streptomyces avermitilis* and derivatives thereof. The morphological characteristics of the culture are completely described in U.S. Pat. No. 4,310,519. The production, isolation, and structure determination of the avermectins are fully described in Albers-Schonberg et al *J. Am. Chem. Soc.* 1981. 103, 4216–4221 and references cited therein. The conversion of natural avermectin $B_1$ to 22,23-dihydro-avermectin $B_1$, the potent broad spectrum anthelminthic agent known as ivermectin, has also been described in the literature (Chabala et al *J. Med. Chem.* 1980, 23, 1134–1136). The naturally occurring avermectins and the instant derivatives thereof have a very high degree of anthelminthic and anti-parasitic activity.

The naturally occurring avermectins are a series of macrocyclic lactones which are substituted at position 13 with a disaccharide consisting of two oleandrose residues. The preparation and properties disaccharide moiety has been removed leaving a free hydroxyl group at position 13 have been described by Mrozik et al *J. Org. Chem.* 1982, 47, 489–492 and by Chabala et al *J. Med. Chem.* 1980, 23, 1134–1136. The natural compounds have the following general structure:

| Compound | broken line | $R_1$ | $R_2$ | $R_3$ |
|---|---|---|---|---|
| $A_{1a}$ | double bond | — | sec-butyl | —$OCH_3$ |
| $A_{1b}$ | double bond | — | iso-propyl | —$OCH_3$ |
| $A_{2a}$ | single bond | —OH | sec-butyl | —$OCH_3$ |
| $A_{2b}$ | single bond | —OH | iso-propyl | —$OCH_3$ |
| $B_{1a}$ | double bond | — | sec-butyl | —OH |
| $B_{1b}$ | double bond | — | iso-propyl | —OH |
| $B_{2a}$ | single bond | —OH | sec-butyl | —OH |
| $B_{2b}$ | single bond | —OH | iso-propyl | —OH |

The avermectins are generally isolated as mixtures of the a and b components (typically $\geq 80\%$ a and $\leq 20\%$ b). Such compounds differ only in the nature of the $R_2$ substituent and this minor structural difference has been found to have very little effect on the chemical reactivity or biological activity of the compounds. Thus although the a and b components can be separated from each other by chromatography this is not necessary and hence is not normally done. The presence of a mixture of a and b components is indicated by dropping the a or b from the designation of the compound. A mixture of avermectin $B_{1a}$ and avermectin $B_{1b}$ is thus referred to as avermectin $B_1$.

A related family of natural products is known as the milbemycins. The milbemycins have the same basic structure as the avermectins but have no substitution at position 13 and have a methyl or ethyl group at position 25 ($R_2$ = methyl or ethyl rather than isopropyl or sec-butyl as in the avermectins). The fermentation conditions used to prepare them are described in U.S. Pat. No. 3,950,360. Closely related 13-deoxyavermectin aglycones are prepared by chemical modification of the natural avermectins and have been

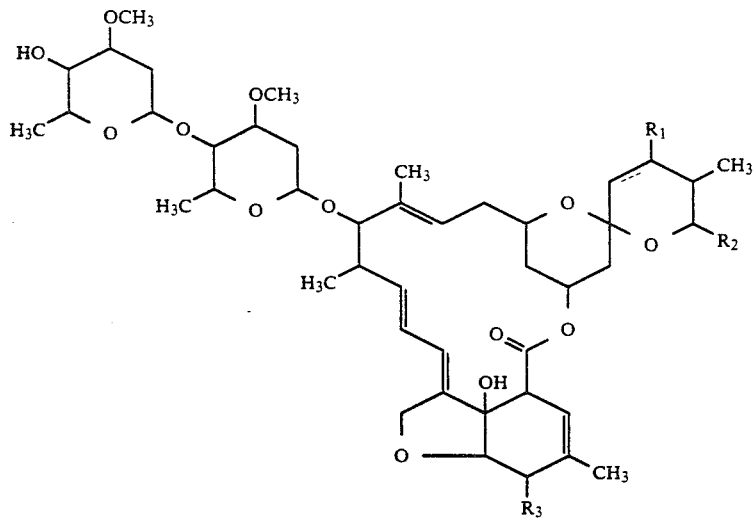

wherein the broken line indicates a single or double bond and;

$R_1$ is hydroxy and is present only when said broken line indicates a single bond;

$R_2$ is iso-propyl or sec-butyl; and $R_3$ is methoxy or hydroxy.

There are eight major natural avermectin compounds, designated $A_{1a}$, $A_{1b}$, $A_{2a}$, $A_{2b}$, $B_{1a}$, $B_{1b}$, $B_{2a}$ and $B_{2b}$. These designations are based on the structure of the individual compounds as shown in the following table (referring to the foregoing structura formula).

described in U.S. Pat. Nos. 4,171,134 and 4,173,571.

Recently a number of related compounds have been described in European Patent Application EPO 170,006 and U.K. aplication 2,166,436 (see also Carter et al, *J. Antibiotics* 1988, 41, 519–529). These compounds are essentially 13-deoxy-avermectin aglycones in which the 25-position side chain contains a double bond and, in some cases, includes additional carbon atoms. In addition, GB 2167751 describes certain 13-substituted milbemycin compounds which are related to the starting materials for the instant compounds.

SUMMARY OF THE INVENTION

This invention is concerned with certain derivatives of avermectin in which a spacer has been introduced between the disaccharide and the aglycone and the use of these derivatives as antiparasitic agents. Thus, it is an object of this invention to describe these avermectin derivatives. A further object of this invention is to describe processes for the preparation of these compounds. A still further object is to describe the use of the instant compounds as antiparasitic agents in the treatment and prevention of parasitic diseases. A still further object is to describe compositions for the treatment of parasitic diseases which contain the novel compounds of this invention as the active ingredient thereof. Further objects will become apparent from a reading of the following description.

DESCRIPTION OF THE INVENTION

The compounds of the instant invention are best realized in the following structure:

wherein:
R is a mono or di-saccharide group;
$X = -(CH_2)_n-$, $-CH_2CH_2OCH_2-$;
$n = 2-5$;
$R_5 = OH$, oxime;
$R_{23} = H$, OH, oxo (OH or oxo only if the broken line is a single bond);
$R_{25} =$ lower alkyl, lower alkenyl;
and the broken line indicates a single or double bond between carbons 22 and 23.

In the instant invention "lower alkyl" is intended to include those alkyl groups of from 1 to 7 carbon atoms in either a straight or branched chain. Examples of such lower alkyl groups are methyl, ethyl, propyl, isopropyl, butyl, sec-butyl, pentyl, hexyl, heptyl, and the like.

The term "lower alkenyl" is intended to include those alkyl groups containing from 1 to 8 carbon atoms in either a straight or branched chain which contains 1 to 2 carbon-carbon double bonds. Examples of such lower alkenyl groups include allyl, butenyl, pentadienyl, hexenyl, and the like.

The term "lower alkanoyl" is intended to include those alkanoyl groups of from 1 to 7 carbon atoms in either a straight or branched chain. Examples of such lower alkanoyl groups are formyl, acetyl, propionyl, isopropionyl, butyryl, pentyryl, and the like.

The term "halide" is intended to include the halogen atoms fluorine, chlorine, bromine, and iodine.

The term "saccharide" is intended to include D- or L-aldohexoses and aldopentoses, commonly known to those skilled in the art as sugars, including those sugars which are partially alkylated and/or partially deoxygenated or in which one or more oxygen atoms have been replaced with nitrogen. Examples of such saccharides are oleandrose, rhamnose, olivose, digitoxose, mycarose, daunosamine, glucose, ribose, galactose, 2-deoxy-ribose, and the like.

Preferred compounds of this invention are realized in the above structural formula when R is the disaccharide group:

and $R_4''$ is OH, $NH_2$, NH(loweralkyl), N(loweralkyl)$_2$, or NH(loweralkanoyl).

More preferred compounds of this invention are realized when:
$X = -(CH_2)_n-$, $-CH_2CH_2OCH_2-$;
$n = 2-5$;
$R_5 = OH$;
$R_4'' = OH$, $NH_2$, NH(lower alkyl), NH(lower alkanoyl);
$R_{23} = H$, OH, oxo (OH or oxo only if the broken line is a single bond);
$R_{25} =$ lower alkyl;
and the broken line indicates a single or double bond between carbons 22 and 23.

Still more preferred compounds of this invention are realized when:
$X = -(CH_2)_n-$;
$n = 2-5$;
$R_5 = OH$;
$R_4'' = OH$, NH(lower alkanoyl);
$R_{23} = H$, OH, (OH only if the broken line is a single bond);
$R_{25} =$ isopropyl or sec-butyl;
and the broken line indicates a single or double bond between carbons 22 and 23.

The most preferred compounds of this invention are realized when:
$X = -(CH_2)_n-$;
$n = 2$ or $3$;
$R_5 = OH$;
$R_4'' = OH$;
$R_{23} = H$;
$R_{25} =$ isopropyl or sec-butyl;
and the broken line indicates a single or double bond between carbons 22 and 23.

Examples of the compounds of this invention are as follows:

13-O-[2-(4'-O-oleandrosyl)-oleandrosyloxyethyl]-avermectin $B_1$ aglycone

13-O-[2-(4'-O-oleandrosyl)-oleandrosyloxyethyl]-avermectin $B_2$ aglycone

13-O-[2-(4'-O-oleandrosyl)-oleandrosyloxyethyl]-22,23-dihydro-avermectin $B_1$ aglycone 13-O-[2-(4'-O-oleandrosyl)-oleandrosyloxyethyl]-13-epi-avermectin $B_1$ aglycone 13-O-[2-(4'-O-oleandrosyl)-oleandrosyloxyethyl]-13-epi-avermectin B$_2$ aglycone 13-O-[2-(4'-O-oleandrosyl)-oleandrosyloxyethyl]-22,23-dihydro-13-epi-avermectin B$_1$ aglycone 13-O-[2-(4'-O-oleandrosyl)-oleandrosyloxyethoxymethyl]-22,23-dihydro-avermectin B$_1$ aglycone 13-O-[3-(4'-O-oleandrosyl)-oleandrosyloxypropyl]-avermectin B$_1$ aglycone 13-O-[3-(4'-O-oleandrosyl)-oleandrosyloxypropyl]-22,23-dihydro-avermectin B$_1$ aglycone 13-O-[2-(4'-O-oleandrosyl)-oleandrosyloxyethyl]-22,23-dihydro-avermectin B$_1$ aglycone-5-oxime 13-O-[2-(4'-O-(4''-amino-4''-deoxy-oleandrosyl))-oleandrosyloxyethyl]-22,23-dihydro-avermectin B$_1$ aglycone 13-O-[2-(4'-O-(4''-amino-4''-deoxy-oleandrosyl))-oleandrosyloxyethyl]-22,23-dihydro-13-epi-avermectin B$_1$ aglycone 13-O-[2-(4'-O-(4''-acetylamino-4''-deoxy-oleandrosyl))-oleandrosyloxyethyl]-22,23-dihydro-avermectin B$_1$ aglycone 13-O-[2-(4'-O-(4''-acetylamino-4''-deoxy-oleandrosyl))-oleandrosyloxyethyl]-22,23-dihydro-13-epi-avermectin B$_1$ aglycone 13-O-[2-(4'-O-(4''-acetylamino-4''-deoxy-oleandrosyl))-oleandrosyloxyethyl]-avermectin B$_1$ aglycone 13-O-[2-(4'-O-(4''-acetylamino-4''-deoxy-oleandrosyl))-oleandrosyloxyethyl]-13-epi-avermectin B$_1$ aglycone 13-O-[2-(4'-O-(4''-acetylamino-4''-deoxy-oleandrosyl))-oleandrosyloxyethyl]-avermectin B$_2$ aglycone 13-O-[2-glucosyloxyethyl]-avermectin B$_1$ aglycone 13-O-[2-rhamnosyloxyethyl]-avermectin B$_1$ aglycone 13-O-[2-oleandrosyloxyethyl]-avermectin B$_2$ aglycone 13-O-[2-oleandrosyloxyethyl]-avermectin B$_2$ aglycone 13-O-[2-galactosyloxyethyl]-avermectin B$_1$ aglycone 13-O-[2-(2'-deoxyribosyl)-oxyethyl]-avermectin B$_1$ aglycone 13-O-[2-oleandrosyloxyethyl]-22,23-dihydro-avermectin B$_1$ aglycone

PREPARATION OF STARTING MATERIALS

The starting materials for this invention are disclosed in Albers-Schonberg et al *J. Am. Chem. Soc.* 1981, 103, 4216–4221 and references cited therein (naturally occurring avermectins), Chabala et al *J. Med. Chem.* 1980, 23, 1134–1136 (22,23-dihydro-avermectin B$_1$ (ivermectin), and 22,23-dihydro-avermectin B$_1$-aglycone), Mrozik et al *J. Org. Chem.* 1982, 47, 489–492 (avermectin aglycones), Blizzard et al *J. Org. Chem.* 1989, 54, 1756–1757 (avermectin disaccharide), Linn et al U.S. Pat. No. 4,587,247 (hydroxyethoxymethyl aglycones) and U.K. application 2,166,436 (compounds with unsaturation in the R$_2$ side chain; see also Carter et al, *J. Antibiotics* 1988, 41, 519–529).

The novel precursors to the compounds of this invention are prepared by procedures outlined in the following reaction schemes:

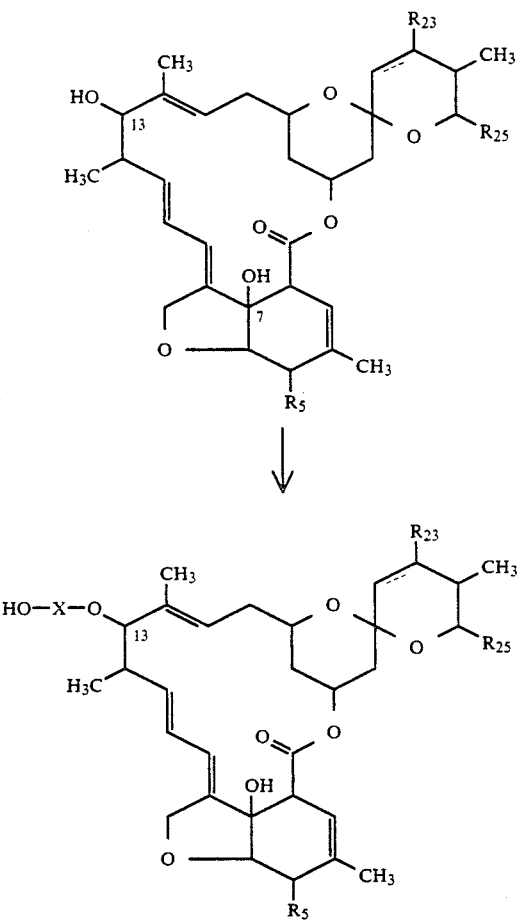

where X, R$_5$, R$_{23}$, and R$_{25}$ are as defined above.

The 13-O-hydroxyalkyl-substituted aglycones which are the precursors of the novel compounds of this invention are prepared from avermectin aglycones by a number of different synthetic routes. During the attachment of the hydroxyalkyl substituent to the C-13-hydroxyl group it is necessary to protect other secondary hydroxyl groups in the molecule (note that it is not necessary to protect the tertiary hydroxyl present at position 7) with a protecting group which may be removed after the reaction is accomplished. Suitable protecting groups include tert-butyldimethylsilyl, tert-butyldiphenylsilyl, phenoxyacetyl, acetyl, and the like. The tert-butyldimethylsilyl group is preferred and is introduced by treating a solution of the alcohol in dimethylformamide (DMF) with an excess of imidazole and a silylating reagent such as tert-butyldimethylsilyl-chloride, tert-butyldimethylsilyl-trifluoromethanesulfonate, and the like at temperatures ranging from 25° C. to 50° C. for 4 to 48 hours. The reaction is then worked up and the product isolated and purified using standard techniques known to those skilled in the art. The protecting group may be removed by treatment with a solution of hydrogen fluoride in a pyridine/tetrahydrofuran solvent mixture. Alternatively, the protecting group may be removed by treatment with a solution of p-toluenesulfonic acid (0.5-2%) in methanol at 0° C. to 25° C. for 0.5 to 8 hours. Deprotection with hydrogen fluoride in pyridine/tetrahydrofuran is preferred. In both cases reaction workup and product isolation and purification are by standard techniques well known to those skilled in the art.

Once all other secondary hydroxyl groups have been protected the hydroxyalkyl substituent may be introduced at position 13. This is accomplished by first converting the 13-hydroxyl group to a better leaving group such as p-toluenesulfonate, iodide, bromide, methanesulfonate, trifluoromethanesulfonate, o-nitro-benzenesulfonate, and the like. Iodide, p-toluenesulfonate, and o-nitro-benzenesulfonate are preferred. The 13-O-p-toluenesulfonate is prepared by reaction of the 13-hydroxyl with a sulfonylating agent such as p-toluenesulfonyl chloride, p-toluenesulfonic anhydride and the like in the presence of a hindered base such as 2,6-lutidine, diisopropylethylamine and the like and a nucleophilic catalyst such as 4-dimethylaminopyridine, 4-pyrrolidinopyridine and the like in a non-nucleophilic solvent such as chloroform, deuterochloroform, dichloromethane, tetrahydrofuran, ether, and the like at temperatures ranging from 0° C. to 35° C. for 1 to 36 hours. Reaction with p-toluenesulfonic anhydride, diisopropylethylamine and 4-dimethylaminopyridine in chloroform is preferred. The reaction may be followed by NMR (if a deuterated solvent is used) or allowed to proceed for a predetermined length of time. The reaction is then worked up and the product isolated using standard techniques known to those skilled in the art. The 13-O-p-toluenesulfonate thus obtained is unstable and is generally used directly without purification. The 13-O-p-toluenesulfonate may be reacted directly with a diol such as ethylene glycol, 1,3-propanediol, 1,4-butanediol and the like to afford the 13-O-hydroxyalkyl substituted avermectin. Alternatively, the 13-O-p-toluenesulfonate may be converted to the more reactive 13-iodide which may then be reacted with a diol such as ethylene glycol, 1,3-propanediol, 1,4-butanediol and the like to afford 13-O-hydroxyalkyl substituted avermectin. The first route (reaction of the diol directly with the p-toluenesulfonate) generally affords 13-O-hydroxylalkyl substituted avermectins with 13-alpha stereochemistry whereas conversion to the iodide followed by reaction of the iodide with a diol generally affords 13-O-hydroxylalkyl substituted avermectins with 13-beta stereochemistry. The 13-O-p-toluenesulfonate may be converted to a (13-alpha)-13-O-hydroxylalkyl substituted avermectin by reaction with an excess of a diol such as ethylene glycol, 1,3-propanediol, 1,4-butanediol and the like in the presence of a base such as potassium acetate, pyridine, sodium hydride and the like either without added solvent or in a non-nucleophilic solvent such as tetrahydrofuran, ether, and the like at temperatures ranging from 25° C. to 75° C. for 1 to 36 hours. For reaction with a liquid diol the use of the diol as the solvent is preferred. The reaction is then worked up and the product is isolated and purified using standard techniques known to those skilled in the art. The 13-O-p-toluenesulfonate may alternatively be converted to a 13(beta)-iodide by reaction with a source of iodide such as potassium iodide, tetrabutylammonium iodide, sodium iodide, and the like in a solvent such as tetrahydrofuran, dimethylformamide, ethyl acetate, dichloromethane, and the like at temperatures ranging from 25° C. to 95° C. for 15 to 120 minutes. Reaction with potassium iodide in dimethylformamide is preferred. The reaction is then worked up and the product is isolated and purified using standard techniques known to those skilled in the art. The resulting 13-beta-iodide may be converted to a 13-beta-hydroxyalkyl substituted avermectin by reaction with an excess of a diol such as ethylene glycol, 1,3-propanediol, 1,4-butanediol and the like in the presence of a hindered base such as 2,6-lutidine, diisopropylethylamine and the like and a silver salt such as silver tetrafluoroborate, silver trifluoromethanesulfonate, and the like in a non-nucleophilic solvent such as tetrahydrofuran, ether, ethyl acetate, and the like at temperatures ranging from 5° C. to 45° C. for 1 to 12 hours. Reaction with a diol and silver tetrafluoroborate in tetrahydrofuran is preferred. The reaction is then worked up and the product is isolated and purified using standard techniques known to those skilled in the art. Alternatively the 13-O-hydroxylalkyl substituted avermectins may be synthesized by reacting an avermectin aglycone with an electrophile such as ethylene oxide, an ethoxy-substituted alkyl iodide, an ethoxy-substituted alkyl trichloracetimidate, and the like in the presence of a base such as pyridine, triethylamine, potassium hydride, and the like (or an acid such as trifluoromethanesulfonic acid in the case where an alkyl trichloracetimidate is the electrophile) in a non-nucleophilic solvent such as tetrahydrofuran, dimethylformamide, dichloromethane and the like at temperatures ranging from 25° C. to 125° C. for 1 to 12 hours. The reaction is then worked up and the product is isolated and purified using standard techniques known to those skilled in the art. This method may be used to prepare 13-O-hydroxyethoxymethyl substituted avermectins which are inaccessible through the alternative route wherein the avermectin aglycone is converted to an electrophile. Thus, reaction of an avermectin aglycone (either 13-alpha or 13-beta stereochemistry) with a protected hydroxyethoxymethyl halide such as 2-acetoxy-ethoxymethyl bromide (see U.S. Pat. No. 4,587,247) in the presence of a hindered base such as diisopropylethylamine, 2,6-lutidine and the like in a non-nucleophilic solvent such as dichloromethane, tetrahydrofuran, ether, and the like at temperatures ranging from 10° C. to 60° C. for 1 to 36 hours. The reaction is then worked up and the product is isolated and purified using standard techniques known to those skilled in the art. The acetate protecting group is then removed by treating a solution of the acetate in a solvent such as methanol, ethanol, and the like with a nucleophilic base such as ammonia, sodium hydroxide, and the like at temperatures ranging from −10° C. to 25° C. for 1 to 6 hours. The reaction is then worked up and the hydroxyethoxymethyl product is isolated and purified using standard techniques known to those skilled in the art. Of course, synthetic routes where the avermectin aglycone serves as a nucleophile will result in 13-O-hydroxyalkyl or hydroxyethoxymethyl avermectins in which the C-13 stereochemistry is preserved. Thus, an avermectin aglycone with 13-alpha stereochemistry will afford a 13-alpha-O-hydroxyalkyl avermectin. If a 13-beta-O-hydroxyalkyl or hydroxyalkoxymethyl avermectin is desired by this route it is necessary to prepare a 13-epi-avermectin aglycone for use as a starting material. The requisite 13-epi-avermectin aglycones may be prepared by inversion of the stereochemistry at position 13 of the corresponding avermectin aglycone (for example, 13-epi-avermectin $B_2$ aglycone is prepared by inversion of position 13 of avermectin $B_2$ aglycone). Preparation of the avermectin aglycones is fully described in the literature references cited above. The inversion may be accomplished by reaction of the above described 13-iodide with water, which may be effected by treating a solution of the iodide in a solvent such as tetrahydrofuran, ether, benzene and the like with water with or without added silver salts such as silver trifluoromethanesulfonate, silver tetrafluoroborate, silver nitrate, and the like at temperatures ranging from 0° C. to the reflux temperature of the solvent for 15 minutes to 24 hours. Conversion of the aglycone to the 13-epi-aglycone by reaction of the 13-tosylate with potassium iodide in dimethylformamide and subsequent solvolysis of the resulting 13-epi-iodide by reaction with water in tetrahydrofuran with added silver trifluoromethanesulfonate or silver tetrafluoroborate is preferred. The reaction is worked up and the 13-epi-aglycone is isolated and purified using standard procedures known to those skilled in the art.

The instant compounds are prepared by attaching a mono- or disaccharide unit to the hydroxyalkyl avermectins. During the attachment of the disaccharide to the 13-O-hydroxyalkyl-substituted aglycone it is necessary to protect secondary (but not tertiary) hydroxyl groups in the molecule as described above. Attachment of the disaccharide may be effected by a variety of glycosylation procedures such as reaction of the aglycone with a glycosyl fluoride or other halide in the presence of one or more salts of various metals such as silver, tin, mercury, copper and the like. An alternative procedure involves reaction of the aglycone with a glycosyl phenylsulfide or a glycosyl pyridylsulfide or a glycosyl phenylsulfoxide in the presence of an activating electrophile such as N-bromosuccinimide, N-iodosuccinimide, trifluoromethane-sulfonic anhydride and the like or metal salts such as silver trifluoromethanesulfonate, silver perchlorate, mercuric nitrate, tin chloride, and the like or a combination of an activating electrophile and a metal salt. Another alternative is reaction of the hydroxyalkyl-avermectin-aglycone with a disaccharide glycal (vinyl ether) and an electrophilic activating agent such as N-iodosuccinimide or an acid such as toluenesulfonic acid, pyridinium toluenesulfonate, and the like may be used.

The process is illustrated in the following reaction scheme:

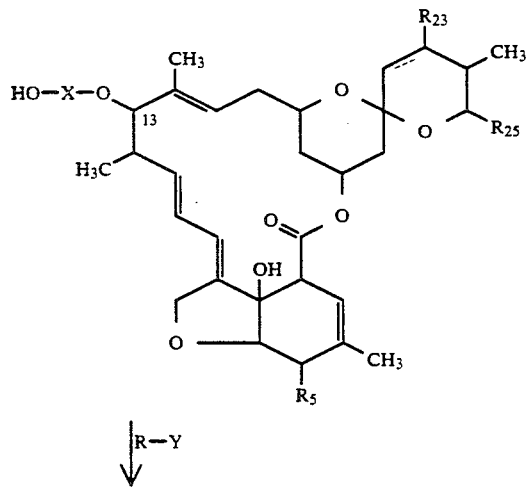

-continued

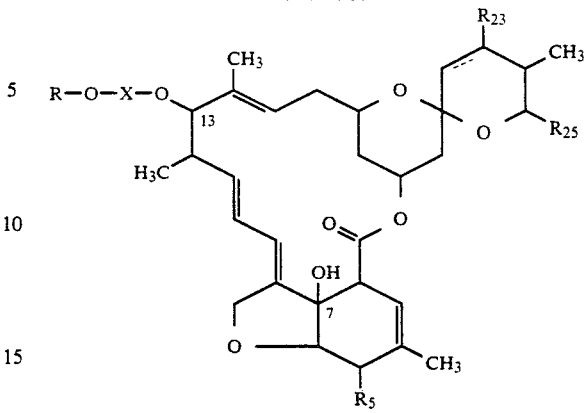

where Y is halogen, pyridylthio, phenylthio, phenylsulfoxy, or phenylsulfonyl and R, X, $R_5$, $R_{23}$, are as defined above (except that free secondary hydroxyl groups are protected as necessary as described above).

Reaction of the aglycone with a glycosyl pyridylsulfide or a glycosyl fluoride is preferred. The glycosyl pyridylsulfide is prepared by treating a solution of the saccharide or disaccharide (free anomeric OH) in a non-nucleophilic solvent such as dichloromethane, chloroform, benzene, toluene, and the like with a dipyridyl disulfide such as 2,2'-dipyridyl disulfide and the like and a tri-aryl or tri-alkyl phosphine such as tributylphosphine or triphenylphosphine, and the like at temperatures ranging from 0° C. to 35° C. for one hour to 48 hours. The reaction is worked up and the glycosyl pyridylsulfide isolated and purified using standard techniques known to those skilled in the art. Reaction of the saccharide or disaccharide with 2,2'-dipyridyl disulfide and tributylphosphine in dichloromethane at room temperature is preferred. The glycosylation reaction is carried out by adding a solution of the glycosyl pyridylsulfide in a non-nucleophilic solvent such as acetonitrile, ether, tetrahydrofuran (THF), chloroform, acetone, and the like to a reaction mixture consisting of a solution of the hydroxyalkyl-avermectin-aglycone in the same solvent and one or more metal salts such as silver trifluoromethanesulfonate, silver perchlorate, tin chloride, tin sulfate, mercuric chloride, copper sulfate, copper bromide, and the like with or without added molecular sieves at temperatures ranging from -20° C. to room temperature for 15 minutes to 48 hours. The reaction is worked up and the product isolated and purified using standard techniques known to those skilled in the art. Reaction of the aglycone and the glycosyl pyridylsulfide in acetonitrile in the presence of silver trifluoromethanesulfonate is preferred. The glycosyl fluoride is prepared by treating a solution of the saccharide or disaccharide (free anomeric OH) in a non-nucleophilic solvent such as dichloromethane, chloroform, and the like with a strong fluorinating agent such as diethylaminosulfur trifluoride (DAST), dimethylaminosulfur trifluoride (methyl DAST), and the like at temperatures ranging from -40° C. to room temperature for 5 minutes to one hour. The reaction is worked up and the glycosyl fluoride isolated and purified using standard techniques known to those skilled in the art. Alternatively, the glycosyl fluoride may be prepared by treating a glycosyl phenylsulfide (prepared by reaction of the disaccharide with phenyl disulfide and tributyl- or triphenyl-phosphine in an inert solvent such as benzene or dichloromethane at room temperature for 1 to 24 hours) with DAST and an electrophilic activating agent such as N-bromosuccinimide, N-iodosuccinimide, and the like in a non-nucleophilic solvent such as dichloromethane, chloroform, and the like at temperatures ranging from −40° C. to room temperature for 5 minutes to one hour. The reaction is worked up and the glycosyl fluoride isolated and purified using standard techniques known to those skilled in the art. Reaction of the saccharide or disaccharide with DAST in dichloromethane at room temperature is preferred. The glycosylation reaction is carried out by adding a solution of the glycosyl fluoride in a non-nucleophilic solvent such as ether, tetrahydrofuran (THF), chloroform, acetone, and the like to a reaction mixture consisting of a solution of the aglycone in the same solvent and one or more metal salts such as silver perchlorate, silver trifluoromethanesulfonate, tin chloride, tin sulfate, mercuric chloride, copper sulfate and the like with or without added molecular sieves at temperatures ranging from −20° C. to room temperature for 15 minutes to 48 hours. The reaction is worked up and the product isolated and purified using standard techniques known to those skilled in the art. Reaction of the aglycone and the glycosyl fluoride in ether in the presence of silver perchlorate, tin (II) chloride, and 3 A molecular sieves is preferred.

In compounds containing the natural avermectin disaccharide (oleandrosyl-oleandrosyl) an amino substituent may be introduced at position 4" by reductive amination of a 4"-ketone which is in turn prepared by oxidation of the 4"-hydroxyl group present in the avermectins. As discussed earlier in connection with the glycosylation reaction, it is also necessary during the oxidation of the hydroxyl group at C-4" to protect other secondary hydroxyl groups in the molecule (note that it is not necessary to protect the tertiary hydroxyl present at position 7) with a protecting group which may be removed after the oxidation is accomplished. Suitable protecting groups include tert-butyldimethylsilyl, tert-butyldiphenylsilyl, phenoxyacetyl, acetyl, and the like. The tert-butyldimethylsilyl group is preferred and is introduced and later removed using the techniques described above.

With other secondary hydroxyl groups protected as a silyl ether the hydroxyl group at position 4" can be oxidized by a variety of methods to afford the ketone derivatives necessary for conversion to amino and acylamino analogs. The oxidation of this hydroxyl group can be effected by using a variety of oxidation procedures, including oxidation with dimethylsulfoxide (DMSO) based systems commonly known to those skilled in the art as Swern (or Moffat) oxidations (DMSO-oxalyl-chloride, DMSO-acetic anhydride, DMSO-trifluoroacetic anhydride and the like) as well as oxidations with chromium based reagents (pyridinium chlorochromate, pyridinium dichromate, and the like), or other methods known to those skilled in the art. The DMSO based oxidations are preferred. The oxidation reagent is generated by treating a solution of DMSO in a non-nucleophilic solvent such as dichloromethane, chlorform, ether (preferred), tetrahydrofuran and the like with an electrophilic activating agent such as oxalyl chloride (preferred), dicyclohexyl-carbodiimide (DCC), phosgene, and the like at temperatures ranging from −90° C. to −55° C. and stirring the mixture thus formed at this temperature for 10 to 90 minutes. To the oxidizing reagent thus generated is added, at the same temperature, a solution of the alcohol in the solvent used to generate the reagent. The solution is stirred at temperatures ranging form −90° C. to −55° C. for 10 to 90 minutes then a hindered base such as triethylamine, diisopropylethylamine, and the like is added. The temperature is raised to 0° C. to 30° C. and the mixture stirred at this temperature for 10 to 90 minutes. The reaction is then worked up and the product isolated and purified using standard techniques known to those skilled in the art.

The 4"-ketone functionality thus generated may be used to introduce amino substituents at position 4" via a reductive amination reaction. The reductive amination is accomplished by treating a solution of the ketone in an alcoholic solvent such as methanol, ethanol, and the like with an ammonium salt such as ammonium acetate (preferred), ammonium formate, ammonium benzoate and the like at temperatures ranging from −25° C. to 25° C. for 15 to 60 minutes then adding sodium cyanoborohydride to the resulting mixture and stirring at temperatures ranging from 0° C. to 30° C. for 30 to 90 minutes. The reaction is then worked up and the product isolated and purified using standard techniques known to those skilled in the art. The reaction may be modified by substituting an alkylammonium salt in the place of ammonium acetate in the above procedure to prepare avermectin derivatives substituted with an alkylamino group at the 4" position.

The amino (or alkylamino) substituted derivatives prepared as described above may be acylated to provide acylamino analogs. The acylation is accomplished by treating a solution of the 4"-amino or 4"-alkylamino analog in a halogenated solvent such as dichloromethane, chloroform or the like with one molar equivalent of an acylating agent such as an alkanoyl chloride (preferred), alkanoyl bromide, alkanoic acid in combination with dicyclohexylcarbodiimide, and the like in the presence of a base such as triethylamine, pyridine and the like with or without the addition of a nucleophilic catalyst such as dimethylaminopyridine at temperatures ranging from −10° C. to 35° C. for 15 minutes to 24 hours. The reaction is then worked up and the product isolated and purified using standard techniques known to those skilled in the art. Note that it is not necessary to protect secondary alcohols in the molecule during the acylation reaction as the amino functionality is sufficiently more reactive that acylation occurs selectively at nitrogen.

Oximes may be generated at position 5 via the 5-ketone. This ketone is prepared by oxidation of a compound with a 5-hydroxyl group using one of the oxidation methods described above. Oxidation with manganese dioxide is preferred. The oxidation is carried out by treating a solution of the alcohol in a non-hydroxylic solvent such as benzene, dichloromethane, chloroform, tetrahydrofuran, and the like with an excess of manganese dioxide at temperatures ranging from 25° C. to the reflux temperature of the solvent for 4 to 48 hours. The reaction is worked up and the product isolated and purified using standard techniques known to those skilled in the art. The ketone thus generated may be used to prepare oximes or alkoximes by a number of procedures. Generally, an excess of hydroxylamine hydrochloride or the appropriate alkoyxlamine hydrochloride (methoxylamine hydrochloride for a methoxime, etc.) is added to a solution of the ketone in pyridine and the solution stirred at temperatures ranging from 0° C. to 50° C. for 3–36 hours. Alternatively the amine hydrochloride is added to a solution of the ketone in a neutral solvent such as benzene, tetrahydrofuran, dioxane, dichloromethane, ethanol, and the like followed by a molar equivalent of a base such as sodium acetate, sodium hydroxide, triethylamine, and the like. The resulting mixture is stirred at temperatures ranging from 0° C. to 50° C. for 3–36 hours. In either case the reaction is worked up and the product isolated and purified using standard techniques known to those skilled in the art.

In the instances where the ultimate precursor is a milbemycin-type compound (lacks substitution at position 13) it is necessary to introduce a hydroxyl group at position 13. This may be accomplished by allylic oxidation of the C-14-15 olefin with selenium dioxide. The oxidation is effected by adding an excess of selenium dioxide to a solution of the olefin in a solvent such as ethanol, methanol, formic acid and the like. The mixture is stirred at temperatures ranging from 25° C. to reflux for 3–36 hours. The reaction is worked up and the product isolated and purified using standard techniques known to those skilled in the art.

The instant compounds of this invention are unexpectedly potent antiparastic agents against endo and ecto parasites, particularly helminths and arthropods, which cause numerous parasitic diseases in humans, animals, and plants.

Parasitic diseases may be caused by either endoparasites or ectoparasites. Endoparasites are those parasites which live inside the body of the host, either within an organ (such as the stomach, lungs, heart, intestines, etc.) or simply under the skin. Ectoparasites are those parasites which live on the outer surface of the host but still draw nutrients from the host.

The endoparasitic diseases generally referred to as helminthiasis are due to infection of the host with parasitic worms known as helminths. Helminthiasis is a prevalent and serious worldwide economic problem due to infection of domesticated animals such as swine, sheep, horses, cattle, goats, dogs, cats, and poultry. Many of these infections are caused by the group of worms described as nematodes which cause diseases in various species of animals throughout the world. These diseases are frequently serious and can result in the death of the infected animal. The most common genera of nematodes infecting the animals referred to above are Haemonchus, Trichostrongylus, Ostertagia, Nematodirus, Cooperia, Ascaris, Bunostomum, Oesophagostomum, Chabertia, Trichuris, Strongylus, Trichonema, Dictyocaulus, Capillaria, Heterakis, Toxocara, Ascaridia, Oxyuris, Ancylostoma, Uncinaria, Toxascaris, and Parascaris. Many parasites are species specific (infect only one host) and most also have a preferred site of infection within the animal. Thus Haemonchus and Ostertagia primarily infect the stomach while Nematodirus and Cooperia mostly attack the intestines. Other parasites prefer to reside in the heart, eyes, lungs, blood vessels, and the like while still others are subcutaneous parasites. Helminthiasis can lead to weakness, weight loss, anemia, intestinal damage, malnutrition, and damage to other organs. If left untreated these diseases can result in the death of the animal.

Infections by ectoparasitic arthropods such as ticks, mites, lice, stable flies, hornflies, blowflies, fleas, and the like are also a serious problem. Infection by these parasites results in loss of blood, skin lesions, and can interfere with normal eating habits thus causing weight loss. These infections can also result in transmission of serious diseases such as encephalitis, anaplasmosis, swine pox, and the like which can be fatal.

Animals may be infected by several species of parasite at the same time since infection by one parasite may weaken the animal and make it more susceptible to infection by a second species of parasite. Thus a compound with a broad spectrum of activity is particularly advantageous in the treatment of these diseases. The compounds of this invention have unexpectedly high activity against these parasites, and in addition are also active against Dirofilaria in dogs, Nematospiroides and Syphacia in rodents, biting insects, and migrating diperous larvae such as Hypoderma sp. in cattle, and Gastrophilus in horses.

The instant compounds are also useful against endo and ecto parasites which cause parasitic diseases in humans. Examples of such endoparasites which infect man include gastro-intestinal parasites of the genera Ancylostoma, Necator, Ascaris, Strongyloides, Trichinella, Capillaria, Trichuris, Enterobius, and the like. Other endoparasites which infect man are found in the blood or in other organs. Examples of such parasites are the filarial worms Wucheria, Brugia, Onchocerca, and the like as well as extra-intestinal stages of the intestinal worms Strongylides and Trichinella. Ectoparasites which parasitize man include arthropods such as ticks, fleas, mites, lice, and the like and, as with domestic animals, infections by these parasites can result in transmission of serious and even fatal diseases. The instant compounds are active against these endo and ecto parasites and in addition are also active against biting insects and other dipterous pests which annoy humans.

The instant compounds are also useful against common household pests such as Blatella sp. (cockroach), Tineola sp. (clothes moth), Attagenus sp. (carpet beetle), *Musca domestica* (housefly) and against *Solenopsis invicta* (imported fire ant).

The compounds are furthermore useful against agricultural pests such as aphids (Acyrthiosiphon sp.), locusts, and boll weevils as well as against insect pests which attack stored grains such as Tribolium sp. and against immature stages of insects living on plant tissue. The compounds are also useful as a nematodicide for the control of soil nematodes which may be agriculturally important.

For use as an antiparasitic agent in animals the instant compounds may be administered internally either orally or by injection, or topically as a liquid drench or as a shampoo.

For oral administration, the compounds may be administered in capsule, tablet, or bolus form or alternatively they can be mixed in the animals feed. The capsules, tablets, and boluses are comprised of the active ingredient in combination with an appropriate carrier vehicle such as starch, talc, magnesium stearate, or di-calcium phosphate. These unit dosage forms are prepared by intimately mixing the active ingredient with suitable finely-powdered inert ingredients including diluents, fillers, disintegrating agents, and/or binders such that a uniform mixture is obtained. An inert ingredient is one that will not react with the instant compounds and which is non-toxic to the animal being treated. Suitable inert ingredients include starch, lactose, talc, magnesium stearate, vegetable gums and oils, and the like. These formulations may contain a widely variable amount of the active and inactive ingredients depending on numerous factors such as the size and type of the animal species to be treated and the type and severity of the infection. The active ingredient may also be administered as an additive to the feed by simply mixing the compound with the feedstuff or by applying the compound to the surface of the feed. Alternatively the active ingredient may be mixed with an inert carrier and the resulting composition may then either be mixed with the feed or fed directly to the animal. Suitable inert carriers include corn meal, citrus meal, fermentation residues, soya grits, dried grains and the like. The active ingredients are intimately mixed with these inert carriers by grinding, stirring, milling, or tumbling such that the final composition contains from 0.001 to 5% by weight of the active ingredient.

The compounds may alternatively be administered parenterally via injection of a formulation consisting of the active ingredient dissolved in an inert liquid carrier. Injection may be either intramuscular, intraruminal, intratracheal, or subcutaneous. The injectable formulation consists of the active ingredient mixed with an appropriate inert liquid carrier. Acceptable liquid carriers include the vegetable oils such as peanut oil, cotton seed oil, sesame oil and the like as well as organic solvents such as solketal, glycerol formal and the like. As an alternative, aqueous parenteral formulations may also be used. The vegetable oils are the preferred liquid carriers. The formulations are prepared by dissolving or suspending the active ingredient in the liquid carrier such that the final formulation contains from 0.005 to 10% by weight of the active ingredient.

Topical application of the instant compounds is possible through the use of a liquid drench or a shampoo containing the instant compounds as an aqueous solution or suspension. These formulations generally contain a suspending agent such as bentonite and normally will also contain an antifoaming agent. Formulations containing from 0.005 to 10% by weight of the active ingredient are acceptable. Preferred formulations are those containing from 0.01 to 5% by weight of the instant compounds.

The instant compounds are primarily useful as antiparasitic agents for the treatment and/or prevention of helminthiasis in domestic animals such as cattle, sheep, horses, dogs, cats, goats, swine, and poultry. They are also useful in the prevention and treatment of parasitic infections of these animals by ectoparasites such as ticks, mites, lice, fleas and the like. They are also effective in the treatment of parasitic infections of humans. In treating such infections the compounds of this invention may be used individually or in combination with each other or with other unrelated antiparasitic agents. The dosage of the instant compounds required for best results depends on several factors such as the species and size of the animal, the type and severity of the infection, the method of administration and the compound used. Oral administration of the instant compounds at a dose level of from 0.0005 to 10 mg per kg of animal body weight, either in a single dose or in several doses spaced a few days apart, generally gives good results. A single dose of one of the instant compounds normally gives excellent control however repeat doses may be given to combat re-infection or for parasite species which are unusually persistent. The techniques for administering these compounds to animals are known to those skilled in the veterinary field.

The compounds of this invention may also be used to combat agricultural pests which attack crops either in the field or in storage. The compounds are applied for such uses as sprays, dusts, emulsions and the like either to the growing plants or the harvested crops. The techniques for applying these compounds in this manner are known to those skilled in the agricultural arts.

The following examples are provided in order that this invention might be more fully understood; they are not to be construed as limitative of the invention. The avermectin derivatives prepared in the following examples are generally isolated as amorphous solids rather than crystalline solids. They are characterized analytically using techniques such as nuclear magnetic resonance, mass spectrometry, and the like. Being amorphous the compounds are not characterized by sharp melting points but the chromatographic and analytical methods employed indicate that they are pure.

EXAMPLE 1

5-O-t-butyldimethylsilyl-22,23-dihydro-avermectin $B_1$ aglycone tert-Butyldimethylsilyl chloride (851 mg) was added to a solution of 22,23-dihydro-avermectin $B_1$ aglycone (3.0 g, prepared as described in Chabala et al., *J. Med. Chem.* 1980, 23, 1134) and imidazole (873 mg) in 10 ml of dry dimethylformamide and the solution stirred at room temperature for 22 hours. The reaction mixture was partitioned between ether (50 ml) and water (100 ml). The aqueous layer was extracted with ether (2×20 ml) and the combined organic layers dried with magnesium sulfate, filtered and evaporated. The crude product was purified on a silica gel column eluted with 12.5% acetone in hexane to afford 1.97 g of a white foam which was identified by $^1$H NMR and mass spectrometry as 5-O-t-butyldimethylsilyl-22,23-dihydro-avermectin $B_1$ aglycone.

EXAMPLE 2

5-O-t-butyldimethylsilyl-avermectin $B_1$-aglycone tert-Butyldimethylsilyl chloride (35 mg) was added to a solution of avermectin $B_1$ aglycone (124 mg, prepared as described in Mrozik et al, *J. Org. Chem.* 1982, 47, 489) and imidazole (36 mg) in 2.5 ml of dry dimethylformamide and the solution stirred at room temperature for 24 hours. The reaction mixture was partitioned between ether (25 ml) and water (25 ml). The aqueous layer was extracted with ether (20 ml) and the combined organic layers dried with magnesium sulfate, filtered and evaporated. The crude product was purified by preparative layer chromatography on a 2.0 mm silica gel plate eluted with 25% acetone in hexane to afford 82 mg of a white foam which was identified by $^1$H NMR and mass spectrometry as 5-O-t-butyldimethylsilyl-avermectin $B_1$ aglycone.

EXAMPLE 3

5,23-bis-O-t-butyldimethylsilyl-avermectin $B_2$-aglycone tert-Butyldimethylsilyl chloride (1.15 g) is added to a solution of avermectin $B_2$ aglycone (2.0 g, prepared as described in prepared as described in Mrozik et al, *J. Org. Chem.* 1982, 47, 489) and imidazole (1.30 g) in 10 ml of dry dimethylformamide and the solution is stirred at room temperature for 22 hours. The reaction mixture is then partitioned between ether (50 ml) and water (100 ml). The aqueous layer is extracted with ether (2×20 ml) and the combined organic layers dried with magnesium sulfate, filtered and evaporated. The crude product is purified on a silica gel column eluted with 12.5% acetone in hexane to afford 5,23-bis-O-t-butyldimethylsilyl-avermectin B$_2$-aglycone which is identified by $^1$H NMR and mass spectrometry.

Elemental analysis: calculated for C$_{46}$H$_{78}$O$_9$Si$_2$: C, 66.46; H, 9.46; Found: C, 66.51; H, 9.80.

EXAMPLE 4

5-O-t-butyldimethylsilyl-13-beta-iodo-13-deoxy-22,23-dihydro-avermectin B$_1$-aglycone A solution of o-nitro-benzenesulfonyl chloride (2.40 g) in 40 ml of dry dichloromethane was added dropwise over a period of 1.5 hours to a solution of 5-O-t-butyldimethylsilyl-22,23-dihydro-avermectin B$_1$ aglycone (2.30 g, Example 1), dimethylaminopyridine (1.7 g), tetrabutylammonium iodide (4.6 g) and diisopropylethylamine (2.77 ml) in 40 ml of dry dichloromethane. The resulting solution was stirred at room temperature for 16.5 hours then partitioned between dichloromethane (20 ml) and 1M aqueous NaH$_2$PO$_4$ (40 ml). The organic layer was washed with 1N HCl (40 ml) and water (40 ml) then dried over MgSO$_4$, filtered, and evaporated. The orange-brown tarry residue was extracted repeatedly with 30 ml portions of hot ether until analytical TLC indicated that all of the product had been extracted. The combined ether extracts were dried over MgSO$_4$, filtered, and evaporated. The residue was purified on a silica gel column eluted with 9% acetone in hexane to afford 1.36 g of a white foam (R$_f$ 0.38) which was identified by $^1$H NMR and mass spectrometry as 5-O-t-butyldimethylsilyl-13-beta-iodo-13-deoxy-22,23-dihydro-avermectin B$_1$-aglycone. An additional 601 mg of impure material was obtained by concentration of fractions containing the product plus impurities.

EXAMPLE 5

5-O-t-butyldimethylsilyl-13-beta-iodo-13-deoxy-avermectin B$_1$-aglycone

Substitution of 5-O-t-butyldimethylsilyl-avermectin B$_1$-aglycone (Example 2) for 5-O-t-butyldimethylsilyl-22,23-dihydro-avermectin B$_1$-aglycone in the procedure described above (Example 4) for the preparation of 5-O-t-butyldimethylsilyl-13-beta-iodo-13-deoxy-22,23-dihydro-avermectin B$_1$-aglycone affords 5-O-t-butyldimethylsilyl-13-beta-iodo-13-deoxy-avermectin B$_1$-aglycone which is identified by $^1$H NMR and mass spectrometry.

EXAMPLE 6

5,23-bis-O-t-butyldimethylsilyl-13-beta-iodo-13-deoxy-avermectin B$_2$-aglycone

Toluenesulfonic anhydride (3.0 g) was added to a solution of 5,23-bis-O-t-butyldimethylsilyl-avermectin B$_2$-aglycone (1.5 g, Example 3), dimethylaminopyridine (1.1 g), and diisopropylethylamine (2.2 ml) in 15 ml of deuterochloroform (note that deuterochloroform is used as the solvent so that the reaction may be followed easily by NMR, alternatively chloroform may be used as the solvent and the reaction allowed to proceed for a predetermined time). The mixture was stirred at room temperature for 16 hours then partitioned quickly between dichloromethane (25 ml) and water (25 ml). The aqueous layer was extracted with dichloromethane (3×25 ml) and the combined organic layers dried over MgSO$_4$, filtered and evaporated. The resulting orange oil was dissolved in 25 ml of dry dimethylformamide then potassium iodide (3.3 g) was added. The mixture was stirred at 60° C. for 75 minutes then cooled to room temperature and partitioned between ether (50 ml) and water (50 ml). The aqueous layer was extracted with ether (3×50 ml) and the combined organic layers dried over MgSO$_4$, filtered and evaporated. The residue was purified on a silica gel column eluted with 4% acetone in hexane to afford 520 mg of a white foam (R$_f$ 0.20) which was identified by $^1$H NMR and mass spectrometry as 5,23-bis-O-t-butyldimethylsilyl-13-beta-iodo-13-deoxy-avermectin B$_2$-aglycone. Elemental analysis: calculated for C$_{46}$H$_{77}$O$_8$Si$_2$I: C, 58.70; H, 8.24; Found: C, 58.79; H, 8.52.

EXAMPLE 7

5-O-t-butyldimethylsilyl-22,23-dihydro-13-epi-avermectin B$_1$-aglycone

Silver trifluoromethanesulfonate (118 mg) was added to a solution of 5-O-t-butyldimethylsilyl-13-beta-iodo-13-deoxy-22,23-dihydro-avermectin B$_1$-aglycone (371 mg, Example 4) and 2,6-lutidine (0.081 ml) in 4 ml of 9:1 tetrahydrofuran:water. The mixture (white precipitate) was stirred at room temperature for 45 minutes then diluted with ether (5 ml) and filtered. Water (3 ml) was added to the filtrate and the pH adjusted to ca. 3 by addition of 2N HCl. The aqueous layer was extracted with ether (3 ml) and the combined organic layers dried over MgSO$_4$, filtered and evaporated. The residue was chromatographed on two 2 mm silica gel plates eluted four times with 33% ether in hexane to afford 144 mg of a white foam (R$_f$ 0.48) which was identified by $^1$H NMR and mass spectrometry as 5-O-t-butyldimethylsilyl-13-epi-22,23-dihydro-avermectin B$_1$-aglycone.

EXAMPLE 8

5-O-t-butyldimethylsilyl-13-epi-avermectin B$_1$-aglycone

Substitution of 5-O-t-butyldimethylsilyl-13-beta-iodo-13-deoxy-avermectin B$_1$-aglycone (Example 5) for 5-O-t-butyldimethylsilyl-13-beta-iodo-13-deoxy-22,23-dihydro-avermectin B$_1$-aglycone in the procedure described above (Example 7) for the preparation of 5-O-t-butyldimethylsilyl-13-epi-22,23-dihydro-avermectin B$_1$-aglycone affords 5-O-t-butyldimethylsilyl-13-epi-avermectin B$_1$-aglycone which is identified by $^1$H NMR and mass spectrometry.

EXAMPLE 9

5,23-bis-O-t-butyldimethylsilyl-13-epi-avermectin B$_2$-aglycone

Silver trifluoromethanesulfonate (410 mg) was added to a solution of 5,23-bis-O-t-butyldimethylsilyl-13-beta-iodo-13-deoxy-avermectin B$_2$-aglycone (520 mg, Example 6) and 2,6-lutidine (0.37 ml) in 9 ml of 9:1 tetrahydrofuran:water. The mixture (yellow-white precipitate) was stirred at room temperature for 45 minutes then partitioned between ether (50 ml) and 0.1N HCl (25 ml). The layers were separated and the organic layer was washed with 25 ml of 5% aqueous NaHCO$_3$ then dried over MgSO$_4$, filtered and evaporated. The residue was chromatographed on four 1.5 mm silica gel plates eluted twice with 33% ether in hexane to afford 280 mg of a white foam (R$_f$ 0.45) which was identified by $^1$H NMR and mass spectrometry as 5,23-bis-O-t-butyldimethylsilyl-13-epi-avermectin B$_2$-aglycone. Elemental analysis: calculated for C$_{46}$H$_{78}$O$_9$Si$_2$: C, 66.46; H, 9.46; Found: C, 66.25; H, 9.20.

EXAMPLE 10

5-O-t-butyldimethylsilyl-13-O-(2-hydroxyethyl)-22,23-dihydro-13-epi-avermectin B₁-aglycone Ethylene glycol (0.030 ml) and 2,6-lutidine (0.040 ml) were added to a solution of 5-O-t-butyldimethylsilyl-13-beta-iodo-13-deoxy-22,23-dihydro-avermectin B₁-aglycone (143 mg, Example 4) in 2 ml of dry tetrahydrofuran then silver tetrafluoroborate (34 mg) was added. The mixture was stirred at room temperature for 3.5 hours then partitioned between ether (5 ml) and 5% aqueous NaHCO₃ (2 ml). The aqueous layer was extracted with ether (3×5 ml) and the combined organic layers were dried over MgSO₄, filtered and evaporated to afford a yellow oil. This crude product was chromatographed on a 1.5 mm silica gel plate eluted with 33% ethyl acetate in hexane to afford 55 mg of a colorless oil ($R_f$ 0.34) which was rechromatographed on a 1.0 mm silica gel plate eluted with 2% methanol in dichloromethane to afford 25 mg of a colorless oil ($R_f$ 0.55) which was identified by ¹H NMR and mass spectrometry as 5-O-t-butyldimethylsilyl-13-O-(2-hydroxyethyl)-22,23-dihydro-13-epi-avermectin B₁-aglycone.

EXAMPLE 11

5-O-t-butyldimethylsilyl-13-O-(2-hydroxyethyl)-13-epi-avermectin B₁-aglycone

Substitution of 5-O-t-butyldimethylsilyl-13-beta-iodo-13-deoxy-avermectin B₁-aglycone (Example 5) for 5-O-t-butyldimethylsilyl-13-beta-iodo-13-deoxy-22,23-dihydro-avermectin B₁-aglycone in the procedure described above (Example 10) for the preparation of 5-O-t-butyldimethylsilyl-13-O-(2-hydroxyethyl)-22,23-dihydro-13-epi-avermectin B₁-aglycone affords 5-O-t-butyldimethylsilyl-13-O-(2-hydroxyethyl)-13-epi-avermectin B₁-aglycone which is identified by ¹H NMR and mass spectrometry.

EXAMPLE 12

5,23-bis-O-t-butyldimethylsilyl-13-O-(2-hydroxyethyl)-13-epi-avermectin B₂-aglycone Substitution of 5,23-bis-O-t-butyldimethylsilyl-13-beta-iodo-13-deoxy-avermectin B₂-aglycone (Example 6) for 5-O-t-butyldimethylsilyl-13-beta-iodo-13-deoxy-22,23-dihydro-avermectin B₁-aglycone in the procedure described above (Example 10) for preparation of 5-O-t-butyldimethylsilyl-13-O-(2-hydroxyethyl)-22,23-dihydro-13-epi-avermectin B₁-aglycone affords 5,23-bis-O-t-butyldimethylsilyl-13-O-(2-hydroxyethyl)-13-epi-avermectin B₂-aglycone which is identified by ¹H NMR and mass spectrometry.

EXAMPLE 13

5-O-t-butyldimethylsilyl-13-O-(3-hydroxypropyl)-22,23-dihydro-13-epi-avermectin B₁-aglycone Substitution of 1,3-propanediol for ethylene glycol in the procedure described above (Example 10) for the preparation of 5-O-t-butyldimethylsilyl-13-O-(2-hydroxyethyl)-22,23-dihydro-13-epi-avermectin B₁-aglycone affords 5-O-t-butyldimethylsilyl-13-O-(3-hydroxypropyl)-22,23-dihydro-13-epi-avermectin B₁-aglycone which is identified by ¹H NMR and mass spectrometry.

EXAMPLE 14

5-O-t-butyldimethylsilyl-13-O-(2-hydroxyethyl)-22,23-dihydro-avermectin B₁-aglycone Diisopropylethylamine (0.75 ml) and 4-dimethylaminopyridine (500 mg) were added to a solution of 5-O-t-butyldimethylsilyl-22,23-dihydro-avermectin B₁-aglycone (500 mg, Example 1) in 3 ml of dry chloroform then p-toluenesulfonic anhydride (865 mg) was added. The resulting dark orange solution was stirred at room temperature overnight then quenched by addition of 3 ml of water. The layers were separated and the aqueous layer was extracted with dichloromethane (3×5 ml). The combined organic layers were dried over MgSO₄, filtered and evaporated to afford a dark orange-brown oil. This crude 13-O-p-toluenesulfonate is unstable and was used without further purification. The crude 13-O-p-toluenesulfonate was dissolved in 2 ml of dry ethylene glycol then potassium acetate (750 mg) was added. The resulting mixture was stirred at 55° C. for 6.5 hours then water (3 ml) was added. The layers were separated and the aqueous layer was extracted with dichloromethane (3×5 ml). The combined organic layers were washed with water (3×15 ml) then dried over MgSO₄, filtered and evaporated to afford a yellow oil. This crude product was chromatographed on a silica gel column eluted with 20% ethyl acetate in hexane to afford 135 mg of a pale yellow oil ($R_f$ 0.34) which was identified by ¹H NMR and mass spectrometry as 5-O-t-butyldimethylsilyl-13-O-(2-hydroxyethyl)-22,23-dihydro-avermectin B₁-aglycone.

EXAMPLE 15

5-O-t-butyldimethylsilyl-13-O-(2-hydroxyethyl)-avermectin B₁-aglycone

Substitution of 5-O-t-butyldimethylsilyl-avermectin B₁-aglycone (Example 2) for 5-O-t-butyldimethylsilyl-22,23-dihydro-avermectin B₁-aglycone in the procedure described above (Example 14) for the preparation of 5-O-t-butyldimethylsilyl-13-O-(2-hydroxyethyl)-22,23-dihydro-avermectin B₁-aglycone affords 5-O-t-butyldimethylsilyl-13-O-(2-hydroxyethyl)-avermectin B₁-aglycone which is identified by ¹H NMR and mass spectrometry.

EXAMPLE 16

5,23-bis-O-t-butyldimethylsilyl-13-O-(2-hydroxyethyl)-avermectin B₂-aglycone

Substitution of 5,23-bis-O-t-butyldimethylsilyl-avermectin B₂-aglycone (Example 3) for 5-O-t-butyldimethylsilyl-22,23-dihydro-avermectin B₁-aglycone in the procedure described above (Example 14) for the preparation of 5-O-t-butyldimethylsilyl-13-O-(2-hydroxyethyl)-22,23-dihydro-avermectin B₁-aglycone affords 5,23-bis-O-t-butyldimethylsilyl-13-O-(2-hydroxyethyl)-avermectin B₂-aglycone which is identified by ¹H NMR and mass spectrometry.

EXAMPLE 17

5-O-t-butyldimethylsilyl-13-O-(3-hydroxypropyl)-22,23-dihydro-avermectin B₁-aglycone Substitution of 1,3-propanediol for ethylene glycol in the procedure described above (Example 14) for the preparation of 5-O-t-butyldimethylsilyl-13-O-(2-hydroxyethyl)-22,23-dihydro-avermectin B₁-aglycone affords 5-O-t-butyldimethylsilyl-13-O-(3-hydroxypropyl)-22,23-dihydro-avermectin B$_1$-aglycone which is identified by $^1$H NMR and mass spectrometry.

EXAMPLE 18

26,27-didehydro-avermectin B$_{2a}$ aglycone

Selenium dioxide (78 mg) is added to a solution of 26,27-didehydro-13-deoxy-avermectin B$_{2a}$ aglycone (100 mg, see Carter et al *J. Antibiotics* 1988, 41, 519–529.) in 4 ml of ethanol and the resulting solution is refluxed for 8 hours. The mixture is partitioned between ether (10 ml) and 5% aqueous sodium bicarbonate (5 ml) and the aqueous layer extracted with ether (3×5 ml). The combined organic layers are dried with magnesium sulfate, filtered and evaporated. The crude product, which consists of a mixture of alcohols, is purified by preparative layer chromatography on a silica gel plate. The band corresponding to the desired product is isolated to afford 26,27-didehydro-avermectin B$_{2a}$ aglycone which is identified by $^1$H NMR and mass spectrometry.

EXAMPLE 19

5,23-bis-O-tert-butyldimethylsilyl-26,27-didehydro-avermectin B$_{2a}$ aglycone

Substitution of 26,27-didehydro-avermectin B$_{2a}$ aglycone (Example 18) for avermectin B$_2$ aglycone in the procedure described above (Example 3) for the preparation of 5,23-bis-O-t-butyldimethylsilyl-avermectin B$_2$ aglycone affords 5,23-bis-O-t-butyldimethylsilyl-26,27-didehydro-avermectin B$_{2a}$ aglycone which is identified by $^1$H NMR and mass spectrometry.

EXAMPLE 20

5,23-bis-O-t-butyldimethylsilyl-13-O-(2-hydroxyethyl)-26,27-didehydro-avermectin B$_2$-aglycone Substitution of 5,23-bis-O-t-butyldimethylsilyl-26,27-didehydro-avermectin B$_2$-aglycone (Example 19) for 5-O-t-butyldimethylsilyl-22,23-dihydro-avermectin B$_1$-aglycone in the procedure described above (Example 14) for the preparation of 5-O-t-butyldimethylsilyl-13-O-(2-hydroxyethyl)-22,23-dihydro-avermectin B$_1$-aglycone affords 5,23-bis-O-t-butyldimethylsilyl-13-O-(2-hydroxyethyl)-26,27-didehydro-avermectin B$_2$-aglycone which is identified by $^1$H NMR and mass spectrometry.

EXAMPLE 21

1'-fluoro-4'-(4"-O-t-butyldimethylsilyl-oleandrosyl)-oleandrose

Diethylaminosulfur trifluoride (0.325 ml) was added to a cold (−20° C.) solution of 686 mg of 4'-(4"-O-t-butyldimethylsilyl-oleandrosyl)-oleandrose (prepared as described in Blizzard et al *J. Org. Chem.* 1989, 54, 1756) in 7 ml of dry dichloromethane. The cold bath was removed and the solution stirred at room temperature for 15 minutes then cooled to 0° C. Methanol (0.5 ml) was added and the solution was stirred at 0° C. for two minutes. Saturated aqueous NaHCO$_3$ (4 ml) was added and the layers were separated. The aqueous layer was extracted with ether (4×4 ml) and the combined organic layers dried over MgSO$_4$, filtered and evaporated. The residue was chromatographed on a silica gel column eluted with 25% ether in hexane to afford 473 mg of a syrup (R$_f$ 0.23) which was identified by $^1$H NMR and mass spectrometry as 1'-fluoro-4'-(4"-O-t-butyldimethylsilyl-oleandrosyl)-oleandrose.

EXAMPLE 22

1'-(2-pyridylthio)-4'-(4"-O-t-butyldimethylsilyl-oleandrosyl)-oleandrose

Tributylphosphine (1.08 ml) was added to a solution of 4'-(4"-O-t-butyldimethylsilyl-oleandrosyl)-oleandrose (1.826 g) and 2,2'-dipyridyl disulfide (956 mg) in 15 ml of dry dichloromethane. The solution was stirred at room temperature for 23 hours then the solvent was evaporated. The residual dark yellow oil was chromatographed on a silica gel column eluted with 20% ethyl acetate in hexane to afford 1.78 g of a colorless syrup (R$_f$ 0.24) which was identified by $^1$H NMR and mass spectrometry as 1'-(2-pyridylthio-4'-(4"-O-t-butyldimethylsilyl-oleandrosyl)-oleandrose (mixture of isomers at C-1', avermectin numbering).

EXAMPLE 23

4",5-bis-O-t-butyldimethylsilyl-13-O-[2-(4'-O-oleandrosyl)-oleandrosyloxyethyl]-22,23-dihydro-13-epi-avermectin B$_1$ aglycone A solution of 160 mg of 1'-fluoro-4'-(4"-O-t-butyldimethylsilyl-oleandrosyl)-oleandrose in 3 ml of dry ether was added dropwise to a cold (0° C.) mixture of 5-O-t-butyldimethylsilyl-13-O-(2-hydroxyethyl)-22,23-dihydro-13-epi-avermectin B$_1$-aglycone (128 mg, Example 10), silver perchlorate (45 mg), tin (II) chloride (41 mg), 3A molecular sieves and 4 ml of dry ether. The resulting mixture was stirred vigorously at 0° C. for 1.5 hours then diluted with ether (3 ml) and centrifuged. The supernatant was decanted and the residue washed with ether (3 ml). The combined supernatants were washed with 5% aqueous NaHCO$_3$ (2 ml) and saturated NaCl (3 ml) then dried over MgSO$_4$, filtered, and evaporated to afford a yellow oil. The residue was chromatographed on three 1.0 mm silica gel plates eluted with 25% acetone in hexane to afford 190 mg of a colorless oil (R$_f$ 0.51) which was identified by $^1$H NMR and mass spectrometry as 4",5-bis-O-t-butyldimethylsilyl-13-O-[2-(4'-O-oleandrosyl)-oleandrosyloxyethyl]-22,23-dihydro-13-epi-avermectin B$_1$ aglycone (mixture of alpha and beta anomers at position 1').

EXAMPLE 24

4",5-bis-O-t-butyldimethylsilyl-13-O-[2-(4'-O-oleandrosyl)-oleandrosyloxyethyl]-22,23-dihydro-avermectin B$_1$ aglycone A solution of 70 mg of 1'-fluoro-4'-(4"-O-t-butyldimethylsilyl-oleandrosyl)-oleandrose in 2 ml of dry ether was added dropwise to a cold (0° C.) mixture of 5-O-t-butyldimethylsilyl-13-O-(2-hydroxyethyl)-22,23-dihydro-avermectin B$_1$-aglycone (50 mg, Example 14), silver perchlorate (17 mg), tin (II) chloride (16 mg), 3 A molecular sieves and 2 ml of dry ether. The resulting mixture was stirred vigorously at 0° C. for 1 hour then diluted with ether (3 ml) and centrifuged. The supernatant was decanted and the residue washed with ether (3 ml). The combined supernatants were washed with 5% aqueous NaHCO$_3$ (2 ml) and saturated NaCl (2 ml) then dried over MgSO$_4$, filtered, and evaporated to afford a yellow oil. The residue was chromatographed on a 1.0 mm silica gel plate eluted with 50% ether in hexane. Two bands were isolated. The first band (R$_f$ 0.53) afforded 17 mg of a colorless oil which was identified by $^1$H NMR and mass spectrometry as 4",5-bis-O-t-butyldimethylsilyl-13-O-[2-(4'-O-oleandrosyl)-oleandrosyloxyethyl]-22,23-dihydro-avermectin $B_1$ aglycone (1'-alpha anomer). The second band ($R_f$ 0.58) afforded 15 mg of a colorless oil which was identified by $^1H$ NMR and mass spectrometry as 4",5-bis-O-t-butyldimethylsilyl-13-O-[2-(4'-O-oleandrosyl)-oleandrosyloxyethyl]-22,23-dihydro-avermectin $B_1$ aglycone (1'-beta anomer).

EXAMPLE 25

4",5-bis-O-t-butyldimethylsilyl-13-O-[2-(4'-O-oleandrosyl)-oleandrosyloxyethyl]-13-epi-avermectin $B_1$ aglycone Substitution of 5-O-t-butyldimethylsilyl-13-O-(2-hydroxyethyl)-13-epi-avermectin $B_1$-aglycone (Example 11) for 5-O-t-butyldimethylsilyl-13-O-(2-hydroxyethyl)-22,23-dihydro-13-epi-avermectin $B_1$-aglycone in the procedure of Example 23 affords 4",5-bis-O-t-butyldimethylsilyl-13-O-[2-(4'-O-oleandrosyl)-oleandrosyloxyethyl]-13-epi-avermectin $B_1$ aglycone (mixture of anomers at position 1') which is identified by $^1H$ NMR and mass spectrometry.

EXAMPLE 26

4",5-bis-O-t-butyldimethylsilyl-13-O-[2-(4'-O-oleandrosyl)-oleandrosyloxyethyl]-avermectin $B_1$ aglycone Substitution of 5-O-t-butyldimethylsilyl-13-O-(2-hydroxyethyl)-avermectin $B_1$-aglycone (Example 15) for 5-O-t-butyldimethylsilyl-13-O-(2-hydroxyethyl)-22,23-dihydro-13-epi-avermectin $B_1$-aglycone in the procedure of Example 23 affords 4",5-bis-O-t-butyldimethylsilyl-13-O-[2-(4'-O-oleandrosyl)-oleandrosyloxyethyl]-avermectin $B_1$ aglycone (mixture of anomers at position 1') which is identified by $^1H$ NMR and mass spectrometry.

EXAMPLE 27

4",5,23-tris-O-t-butyldimethylsilyl-13-O-[2-(4'-O-oleandrosyl)-oleandrosyloxyethyl]-13-epi-avermectin $B_2$ aglycone Substitution of 5,23-bis-O-t-butyldimethylsilyl-13-O-(2-hydroxyethyl)-13-epi-avermectin $B_2$-aglycone (Example 12) for 5-O-t-butyldimethylsilyl-13-O-(2-hydroxyethyl)-22,23-dihydro-13-epi-avermectin $B_1$-aglycone in the procedure of Example 23 affords 4",5,23-tris-O-t-butyldimethylsilyl-13-O-[2-(4'-O-oleandrosyl)-oleandrosyloxyethyl]-13-epi-avermectin $B_2$ aglycone (mixture of anomers at position 1') which is identified by $^1H$ NMR and mass spectrometry.

EXAMPLE 28

4",5,23-tris-O-t-butyldimethylsilyl-13-O-[2-(4'-O-oleandrosyl)-oleandrosyloxyethyl]-avermectin $B_2$ aglycone Substitution of 5,23-bis-O-t-butyldimethylsilyl-13-O-(2-hydroxyethyl)-avermectin $B_2$-aglycone (Example 16) for 5-O-t-butyldimethylsilyl-13-O-(2-hydroxyethyl)-22,23-dihydro-13-epi-avermectin $B_1$-aglycone in the procedure of Example 23 affords 4",5,23-tris-O-t-butyldimethylsilyl-13-O-[2-(4'-O-oleandrosyl)-oleandrosyloxyethyl]-avermectin $B_2$ aglycone (mixture of anomers at position 1') which is identified by $^1H$ NMR and mass spectrometry.

EXAMPLE 29

4",5-bis-O-t-butyldimethylsilyl-13-O-[3-(4'-O-oleandrosyl)-oleandrosyloxypropyl]-22,23-dihydro-13-epi-avermectin $B_1$ aglycone Substitution of 5-O-t-butyldimethylsilyl-13-O-(3-hydroxypropyl)-22,23-dihydro-13-epi-avermectin $B_1$-aglycone (Example 13) for 5-O-t-butyldimethylsilyl-13-O-(2-hydroxyethyl)-22,23-dihydro-13-epi-avermectin $B_1$-aglycone in the procedure of Example 23 affords 4",5-bis-O-t-butyldimethylsilyl-13-O-[3-(4'-O-oleandrosyl)-oleandrosyloxypropyl]-22,23-dihydro-13-epi-avermectin $B_1$ aglycone (mixture of anomers at position 1') which is identified by $^1H$ NMR and mass spectrometry.

EXAMPLE 30

4",5-bis-O-t-butyldimethylsilyl-13-O-[3-(4'-O-oleandrosyl)-oleandrosyloxypropyl]-22,23-dihydro-avermectin $B_1$ aglycone Substitution of 5-O-t-butyldimethylsilyl-13-O-(3-hydroxypropyl)-22,23-dihydro-avermectin $B_1$-aglycone (Example 17) for 5-O-t-butyldimethylsilyl-13-O-(2-hydroxyethyl)-22,23-dihydro-13-epi-avermectin $B_1$-aglycone in the procedure of Example 23 affords 4",5-bis-O-t-butyldimethylsilyl-13-O-[3-(4'-O-oleandrosyl)-oleandrosyloxypropyl]-22,23-dihydro-avermectin $B_1$ aglycone (mixture of anomers at position 1') which is identified by $^1H$ NMR and mass spectrometry.

EXAMPLE 31

4",5,23-tris-O-t-butyldimethylsilyl-13-O-[2-(4'-O-oleandrosyl)-oleandrosyloxyethyl]-26,27-didehydro-avermectin $B_2$ aglycone Substitution of 5,23-bis-O-t-butyldimethylsilyl-13-O-(2-hydroxyethyl)-26,27-didehydro-avermectin $B_2$-aglycone (Example 20) for 5-O-t-butyldimethylsilyl-13-O-(2-hydroxyethyl)-22,23-dihydro-13-epi-avermectin $B_1$-aglycone in the procedure of Example 23 affords 4",5,23-tris-O-t-butyldimethylsilyl-13-O-[2-(4'-O-oleandrosyl)-oleandrosyloxyethyl]-26,27-didehydro-avermectin $B_2$ aglycone (mixture of anomers at position 1') which is identified by $^1H$ NMR and mass spectrometry.

EXAMPLE 32

4",5-bis-O-t-butyldimethylsilyl-13-O-[2-(4'-O-oleandrosyl)-oleandrosyloxyethoxymethyl]-22,23-dihydro-avermectin $B_1$ aglycone A solution of silver trifluoromethanesulfonate (345 mg) in 0.50 ml of dry acetonitrile was added slowly dropwise (over a period of 30 minutes) to rapidly stirring solution of 5-O-t-butyldimethylsilyl-13-O-[2-hydroxyethoxymethyl]-22,23-dihydro-avermectin $B_1$ aglycone (800 mg, prepared as desscribed in U.S. Pat. No. 4,587,247) and 1'-(2-pyridylthio)-4'-(4"-O-t-butyldimethylsilyl-oleandrosyl)-oleandrose (800 mg, Example 22) in 1.5 ml of dry acetonitrile. The resulting mixture was stirred vigorously at room temperature for 10 minutes then partitioned between ethyl acetate (10 ml) and 5% aqueous $NaHCO_3$ (8 ml). The layers were separated with the aid of a centrifuge. The aqueous layer was extracted with ethyl acetate (4×4 ml). The combined organic layers were dried over $MgSO_4$ and $K_2CO_3$, filtered, and evaporated to a yellow foam. This crude product was chromatographed on a silica gel column eluted with 12.5% acetone in hexane to afford 714 mg of a white foam (R$_f$ 0.25) which was identified by $^1$H NMR and mass spectrometry as 4",5-bis-O-t-butyldimethylsilyl-13-O-[2-(4'-O-oleandrosyl)-oleandrosyloxyethoxymethyl]-22,23-dihydro-avermectin B$_1$ aglycone (mixture of anomers at position 1').

EXAMPLE 33

13-O-[2-(4'-O-oleandrosyl)-oleandrosyloxyethyl]-22,23-dihydro-13-epi-avermectin B$_1$ aglycone A deprotection reagent solution was prepared by cautiously adding 25 g of hydrogen fluoride.-pyridine complex (Aldrich Chemical Co.) to a cold (0° C.) mixture of pyridine (10 ml) and tetrahydrofuran (27.5 ml). A portion (1 ml) of the resulting reagent solution was added to a cold (0° C.) solution of 200 mg of 4",5-bis-O-t-butyldimethylsilyl-13-O-[2-(4'-O-oleandrosyl)-oleandrosyloxyethyl]-22,23-dihydro-13-epi-avermectin B$_1$ aglycone (mixture of anomers at position 1', Example 23) in 1 ml of dry tetrahydrofuran. The resulting solution was stirred at room temperature for 25 hours then cooled in an ice bath as ether (5 ml) and 1N HCl (2 ml) were added. The layers were separated and the aqueous layer was extracted with ether (3×5 ml). The combined organic layers were dried over MgSO$_4$, filtered and evaporated to a pale yellow oil (175 mg). The crude product was chromatographed on three 1.0 mm silica gel plates eluted three times with 25% acetone in hexane. Three bands were isolated. The first band (R$_f$ 0.50) afforded 20 mg of a colorless oil which was identified by $^1$H NMR and mass spectrometry as recovered 4",5-bis-O-t-butyldimethylsilyl-13-O-[2-(4'-O-oleandrosyl)-oleandrosyloxyethyl]-22,23-dihydro-13-epi-avermectin B$_1$ aglycone (mixture of anomers at position 1'). The second band (R$_f$ 0.33) afforded 52 mg of a colorless oil which was identified by $^1$H NMR and mass spectrometry as 13-O-[2-(4'-O-oleandrosyl)-oleandrosyloxyethyl]-22,23-dihydro-13-epi-avermectin B$_1$ aglycone (1'-alpha isomer; Elemental analysis: calculated for C$_{50}$H$_{78}$O$_{15}$: C, 65.34; H, 8.55; found: C, 64.93; H, 8.64.). The third band (R$_f$ 0.27) afforded 54 mg of a colorless oil which was identified by $^1$H NMR and mass spectrometry as 13-O-[2-(4'-O-oleandrosyl)-oleandrosyloxyethyl]-22,23-dihydro-13-epi-avermectin B$_1$ aglycone (1'-beta isomer; Elemental analysis: calculated for C$_{50}$H$_{78}$O$_{15}$: C, 65.34; H, 8.55; found: C, 64.90; H, 8.64.).

EXAMPLE 34

13-O-[2-(4'-O-oleandrosyl)-oleandrosyloxyethyl]-22,23-dihydro-avermectin B$_1$ aglycone (1'-alpha anomer)

A deprotection reagent solution was prepared by cautiously adding 25 g of hydrogen fluoride.-pyridine complex (Aldrich Chemical Co.) to a cold (0° C.) mixture of pyridine (10 ml) and tetrahydrofuran (27.5 ml). A portion (0.5 ml) of the resulting reagent solution was added to a cold (0° C.) solution of 200 mg of 4",5-bis-O-t-butyldimethylsilyl-13-O-[2-(4'-O-oleandrosyl)-oleandrosyloxyethyl]-22,23-dihydro-avermectin B$_1$ aglycone (Example 24, 1'-alpha anomer) in 0.5 ml of dry tetrahydrofuran. The resulting solution was stirred at room temperature for 19 hours then cooled in an ice bath as ether (4 ml) and 5% aqueous NaHCO$_3$ (2 ml) were added. The pH of the aqueous layer was adjusted to ca. 8–9 by addition of 5N NaOH. The layers were separated and the aqueous layer was extracted with ether (2×5 ml). The combined organic layers were dried over MgSO$_4$ and K$_2$CO$_3$, filtered and evaporated to a colorless oil. The crude product was chromatographed on a 0.5 mm silica gel plate eluted with 33% acetone in hexane to afford 25 mg of a colorless oil (Rf 0.30) which was identified by $^1$H NMR and mass spectrometry as 13-O-[2-(4'-O-oleandrosyl)-oleandrosyloxyethyl]-22,23-dihydro-13-epi-avermectin B$_1$ aglycone (1'-alpha isomer; Elemental analysis: calculated for C$_{50}$H$_{78}$O$_{15}$: C, 65.34; H, 8.55; found: C, 64.91; H, 8.43).

EXAMPLE 35

13-O-[2-(4'-O-oleandrosyl)-oleandrosyloxyethyl]-22,23-dihydro-avermectin B$_1$ aglycone (1'-beta anomer)

A deprotection reagent solution was prepared by cautiously adding 25 g of hydrogen fluoride.-pyridine complex (Aldrich Chemical Co.) to a cold (0° C.) mixture of pyridine (10 ml) and tetrahydrofuran (27.5 ml). A portion (0.5 ml) of the resulting reagent solution was added to a cold (0° C.) solution of 200 mg of 4",5-bis-O-t-butyldimethylsilyl-13-O-[2-(4'-O-oleandrosyl)-oleandrosyloxyethyl]-22,23-dihydro-avermectin B$_1$ aglycone (Example 24, 1'-betanomer) in 0.5 ml of dry tetrahydrofuran. The resulting solution was stirred at room temperature for 18.5 hours then cooled in an ice bath as ether (4 ml) and 5% aqueous NaHCO$_3$ (2 ml) were added. The pH of the aqueous layer was adjusted to ca. 8–9 by addition of 5N NaOH. The layers were separated and the aqueous layer was extracted with ether (2×5 ml). The combined organic layers were dried over MgSO$_4$ and K$_2$CO$_3$, filtered and evaporated to a colorless oil. The crude product was chromatographed on a 0.5 mm silica gel plate eluted with 33% acetone in hexane to afford 25 mg of a colorless oil (Rf 0.25) which was identified by $^1$H NMR and mass spectrometry as 13-O-[2-(4'-O-oleandrosyl)-oleandrosyloxyethyl]-22,23-dihydro-13-epi-avermectin B$_1$ aglycone (1'-beta isomer; Elemental analysis: calculated for C$_{50}$H$_{78}$O$_{15}$.0.6H$_2$O: C, 64.58; H, 8.58; found: C, 64.51; H, 8.28).

EXAMPLE 36

13-O-[2-(4'-O-oleandrosyl)-oleandrosyloxyethoxymethyl]-22,23-dihydro-avermectin B$_1$ aglycone A deprotection reagent solution was prepared by cautiously adding 25 g of hydrogen fluoride.-pyridine complex (Aldrich Chemical Co.) to a cold (0° C.) mixture of pyridine (12.5 ml) and tetrahydrofuran (27.5 ml). A portion (3 ml) of the resulting reagent solution was added to a cold (0° C.) solution of 714 mg of 4",5-bis-O-t-butyldimethylsilyl-13-O-[2-(4'-O-oleandrosyl)-oleandrosyloxyethoxymethyl]-22,23-dihydro-avermectin B$_1$ aglycone (Example 32, mixture of anomers at position 1') in 6 ml of dry tetrahydrofuran. The resulting solution was stirred at room temperature for 63 hours then cooled in an ice bath as pyridine (6 ml), ethyl acetate (8 ml) and 5% aqueous NaHCO$_3$ (12 ml) were added. The layers were separated and the aqueous layer was extracted with ethyl acetate (4×15 ml). The combined organic layers were dried over MgSO$_4$ and K$_2$CO$_3$, filtered and evaporated to a yellow oil. The crude product was chromatographed on five 1.5 mm silica gel plates eluted with tert-butyl methyl ether to afford 320 mg of a colorless oil (R$_f$ 0.44) which was identified by $^1$H NMR and pass spectrometry as 13-O-[2-(4'-O-oleandrosyl)-oleandrosyloxyethoxymethyl]-22,23-dihydro-avermectin B$_1$ aglycone (mixture of anomers at position 1'). The anomers were separated by preparative HPLC on a Whatman M-20 Partisil 10 ODS-3 (reverse phase) column eluted with 20% water in methanol. Two fractions were collected. The first fraction afforded 85 mg of a white amorphous solid (retention time 44.0 minutes on a Whatman Partisil 10 ODS-3 analytical column eluted with 1 ml/minute of 20% water in methanol) which was identified by $^1$H NMR and mass spectrometry as 13-O-[2-(4'-O-oleandrosyl)-oleandrosyloxyethoxymethyl]-22,23-dihydro-avermectin $B_1$ aglycone (1'-beta anomer). The second fraction afforded 165 mg of a white amorphous solid (retention time 54.9 minutes on a Whatman Partisil 10 ODS-3 analytical column eluted with 1 ml/minute of 20% water in methanol) which was identified by $^1$H NMR and mass spectrometry as 13-O-[2-(4'-O-oleandrosyl)-oleandrosyloxyethoxymethyl]-22,23-dihydro-avermectin $B_1$ aglycone (1'-alpha anomer).

EXAMPLE 37

13-O-[2-(4'-O-oleandrosyl)-oleandrosyloxyethyl]-13-epi-avermectin $B_1$ aglycone Substitution of 4",5-O-t-butyldimethylsilyl-13-O-[2-(4'-O-oleandrosyl)-oleandrosyloxyethyl]-13-epi-avermectin $B_1$ aglycone (Example 25) for 4",5-bis-O-t-butyldimethylsilyl-13-O-[2-(4'-O-oleandrosyl)-oleandrosyloxyethoxymethyl]-22,23-dihydro-avermectin $B_1$ aglycone in the deprotection procedure of Example 36 affords 13-O-[2-(4'-O-oleandrosyl)-oleandrosyloxyethyl]-13-epi-avermectin $B_1$ aglycone which is identified by $^1$H NMR and mass spectrometry.

EXAMPLE 38

13-O-[2-(4'-O-oleandrosyl)-oleandrosyloxyethyl]-avermectin $B_1$ aglycone

Substitution of 4",5-bis-O-t-butyldimethylsilyl-13-O-[2-(4'-O-oleandrosyl)-oleandrosyloxyethyl]-avermectin $B_1$ aglycone (Example 26) for 4",5-bis-O-t-butyldimethylsilyl-13-O-[2-(4'-O-oleandrosyl)-oleandrosyloxyethoxymethyl]-22,23-dihydro-avermectin $B_1$ aglycone in the deprotection procedure of Example 36 affords 13-O-[2-(4'-O-oleandrosyl)-oleandrosyloxyethyl]-avermectin $B_1$ aglycone which is identified by $^1$H NMR and mass spectrometry.

EXAMPLE 39

13-O-[2-(4'-O-oleandrosyl)-oleandrosyloxyethyl]-13-epi-avermectin $B_2$ aglycone Substitution of 4",5,23-tris-O-t-butyldimethylsilyl-13-O-[2-(4'-O-oleandrosyl)-oleandrosyloxyethyl]-13-epi-avermectin $B_2$ aglycone (Example 27) for 4",5-bis-O-t-butyldimethylsilyl-13-O-[2-(4'-O-oleandrosyl)-oleandrosyloxyethoxymethyl]-22,23-dihydro-avermectin $B_1$ aglycone in the deprotection procedure of Example 36 affords 13-O-[2-(4'-O-oleandrosyl)-oleandrosyloxyethyl]-13-epi-avermectin $B_2$ aglycone which is identified by $^1$H NMR and mass spectrometry.

EXAMPLE 40

13-O-[2-(4'-O-oleandrosyl)-oleandrosyloxyethyl]-avermectin $B_2$ aglycone

Substitution of 4",5,23-tris-O-t-butyldimethylsilyl-13-O-[2-(4'-O-oleandrosyl)-oleandrosyloxyethyl]-avermectin $B_2$ aglycone (Example 28) for 4",5-bis-O-t-butyldimethylsilyl-13-O-[2-(4'-O-oleandrosyl)-oleandrosyloxyethoxymethyl]-22,23-dihydro-avermectin $B_1$ aglycone in the deprotection procedure of Example 36 affords 13-O-[2-(4'-O-oleandrosyl)-oleandrosyloxyethyl]-avermectin $B_2$ aglycone which is identified by $^1$H NMR and mass spectrometry.

EXAMPLE 41

13-O-[3-(4'-O-oleandrosyl)-oleandrosyloxypropyl]-22,23-dihydro-13-epi-avermectin $B_1$ aglycone Substitution of 4",5-bis-O-t-butyldimethylsilyl-13-O-[3-(4'-O-oleandrosyl)-oleandrosyloxypropyl]-22,23-dihydro-13-epi-avermectin $B_1$ aglycone (Example 29) for 4",5-bis-O-t-butyldimethylsilyl-13-O-[2-(4'-O-oleandrosyl)-oleandrosyloxyethoxymethyl]-22,23-dihydro-avermectin $B_1$ aglycone in the deprotection procedure of Example 36 affords 13-O-[3-(4'-O-oleandrosyl)-oleandrosyloxypropyl]-22,23-dihydro-13-epi-avermectin $B_1$ aglycone which is identified by $^1$H NMR and mass spectrometry.

EXAMPLE 42

13-O-[3-(4'-O-oleandrosyl)-oleandrosyloxypropyl]-22,23-dihydro-avermectin $B_1$ aglycone Substitution of 4",5-bis-O-t-butyldimethylsilyl-13-O-[3-(4'-O-oleandrosyl)-oleandrosyloxypropyl]-22,23-dihydro-avermectin $B_1$ aglycone (Example 30) for 4",5-bis-O-t-butyldimethylsilyl-13-O-[2-(4'-O-oleandrosyl)-oleandrosyloxyethoxymethyl]-22,23-dihydro-avermectin $B_1$ aglycone in the deprotection procedure of Example 36 affords 13-O-[3-(4'-O-oleandrosyl)-oleandrosyloxypropyl]-22,23-dihydro-avermectin $B_1$ aglycone which is identified by $^1$H NMR and mass spectrometry.

EXAMPLE 43

13-O-[2-(4'-O-oleandrosyl)-oleandrosyloxyethyl]-26,27-didehydro-avermectin $B_2$ aglycone Substitution of 4",5,23-tris-O-t-butyldimethylsilyl-13-O-[2-(4'-O-oleandrosyl)-oleandrosyloxyethyl]-26,27-didehydro-avermectin $B_2$ aglycone (Example 31) for 4",5-bis-O-t-butyldimethylsilyl-13-O-[2-(4'-O-oleandrosyl)-oleandrosyloxyethoxymethyl]-22,23-dihydro-avermectin $B_1$ aglycone in the deprotection procedure of Example 36 affords 13-O-[2-(4'-O-oleandrosyl)-oleandrosyloxyethyl]-26,27-didehydro-avermectin $B_2$ aglycone which is identified by $^1$H NMR and mass spectrometry.

EXAMPLE 44

5-oxo-13-O-[2-(4'-O-oleandrosyl)-oleandrosyloxyethyl]-22,23-dihydro-13-epi-avermectin $B_1$ aglycone (1'-beta anomer)

Manganese dioxide (65 mg) is added to a solution of 100 mg of 13-O-[2-(4'-O-oleandrosyl)oleandrosyloxyethyl]-22,23-dihydro-13-epi-avermectin $B_1$ aglycone (1'-beta anomer, Example 35) in 5 ml of dry benzene. The resulting mixture is stirred at 35° C. until complete by analytical thin layer chromatography. The mixture is partitioned between water (5 ml) and ether (5 ml) and the aqueous layer extracted with ether (3×5 ml). The combined organic layers are dried over $MgSO_4$, filtered, and evaporated. The crude product is chromatographed on a silica gel plate to afford 5-oxo-13-O-[2-(4'-O-oleandrosyl)-oleandrosyloxyethyl]-22,23-dihydro-13-epi-avermectin $B_1$ aglycone (1'-beta anomer) which is identified by $^1$H NMR and mass spectrometry.

EXAMPLE 45

13-O-[2-(4'-O-oleandrosyl)-oleandrosyloxyethyl]-22,23-dihydro-13-epi-avermectin B₁ aglycone-5-oxime (1'-beta anomer)

Hydroxylamine hydrochloride (50 mg) is added to a solution of 5-oxo-13-O-[2-(4'-O-oleandrosyl)-oleandrosyloxyethyl]-22,23-dihydro-13-epi-avermectin B₁ aglycone (1'-beta anomer) (75 mg, Example 44) in 3 ml of dry pyridine. The solution is stirred at room temperature until complete by analytical thin layer chromatography. The mixture is partitioned between water (7 ml) and ether (7 ml) and the aqueous layer extracted with ether (3×5 ml). The combined organic layers are dried over MgSO₄, filtered, and evaporated. The crude product is chromatographed on a silica gel plate to afford 13-O-[2-(4'-O-oleandrosyl)-oleandrosyloxyethyl]-22,23-dihydro-13-epi-avermectin B₁ aglycone-5-oxime (1'-beta anomer) which is identified by ¹H NMR and mass spectrometry.

EXAMPLE 46

5-O-t-butyldimethylsilyl-13-O-[2-(4'-O-oleandrosyl)-oleandrosyloxyethyl]-22,23-dihydro-13-epi-avermectin B₁ aglycone (1'-beta isomer)

tert-Butyldimethylsilyl chloride (30 mg) is added to a solution of 13-O-[2-(4'-O-oleandrosyl)-oleandrosyloxyethyl]-22,23-dihydro-13-epi-avermectin B₁ aglycone (1'-beta isomer, Example 35) (100 mg) and imidazole (27 mg) in 1.5 ml of dry tetrahydrofuran and the solution is stirred at 45° C. for 5 hours. The reaction mixture is quenched be addition of 0.2 ml of methanol then concentrated under vacuum. The residue is partitioned between dichloromethane (5 ml) and water (5 ml). The aqueous layer is extracted with dichloromethane (5 ml) and the combined organic layers are washed with saturated aqueous NaCl then dried over magnesium sulfate, filtered and evaporated. The crude product is chromatographed on a 1.0 mm silica gel plate eluted with 25% acetone in hexane to afford 5-O-t-butyldimethylsilyl-13-O-[2-(4'-O-oleandrosyl)-oleandrosyloxyethyl]-22,23-dihydro-13-epi-avermectin B₁ aglycone (1'-beta isomer) which is identified by ¹H NMR and mass spectrometry.

EXAMPLE 47

5-O-t-butyldimethylsilyl-13-O-[2-(4'-O-oleandrosyl)-oleandrosyloxyethyl]-avermectin B₁ aglycone Substitution of 13-O-[2-(4'-O-oleandrosyl)-oleandrosyloxyethyl]-avermectin B₁ aglycone (Example 38) for 13-O-[2-(4'-O-oleandrosyl)-oleandroxyloxyethyl]-22,23-dihydro-13-epi-avermectin B₁ aglycone in the procedure of Example 46 affords 5-O-t-butyldimethylsilyl-13-O-[2-(4'-O-oleandrosyl)-oleandrosyloxyethyl]-avermectin B₁ aglycone which is identified by ¹H NMR and mass spectrometry.

EXAMPLE 48

5-O-t-butyldimethylsilyl-4"-amino-4"-deoxy-13-O-[2-(4'-O-oleandrosyl)-oleandrosyloxyethyl]-22,23-dihydro-13-epi-avermectin B₁ aglycone Oxalyl chloride (0.022 ml) is added to a cold (−78° C.) solution of DMSO (0.042 ml) in 2 ml of dry dichloromethane and the resulting solution is stirred for 20 minutes at −78° C. A solution of 5-O-t-butyldimethylsilyl-13-O-[2-(4'-O-oleandrosyl)-oleandrosyloxyethyl]-22,23-dihydro-13-epi-avermectin B₁ aglycone (80 mg, Example 46) in 2 ml of dry dichloromethane is then added. The resulting mixture is stirred at −78° C. for 1 hour then triethylamine (0.115 ml) is added and the cold bath is removed. The mixture is allowed to warm to room temperature and is stirred at room temperature for 1 hour. The mixture is diluted with dichloromethane (3 ml) then water (5 ml) is added and the layers are separated. The aqueous layer is extracted with dichloromethane (3×5 ml) and the combined organic layers are dried over MgSO₄, filtered and evaporated. This crude oxidation product (5-O-t-butyldimethylsilyl-4"-oxo-13-O-[2-(4'-O-oleandrosyl)-oleandrosyloxyethyl]-22,23-dihydro-13-epi-avermectin B₁ aglycone) is dissolved in 2 ml of dry methanol then 3 A molecular sieves are added followed by ammonium acetate (62 mg). The mixture is stirred at room temperature for 30 minutes then sodium cyanoborohydride (18 mg) is added in two portions (ca. 10 minutes apart). The mixture is stirred at room temperature for 2 hours then centrifuged. The supernatant is decanted and the solid residue is washed with dichloromethane (2×3 ml). The combined supernatants are added to 3 ml of 5% aqueous NaHCO₃. The layers are separated and the aqueous layer is extracted with dichloromethane (2×3 ml). The combined organic layers are dried over MgSO₄, filtered and evaporated. The residue is chromatographed on a silica gel column to afford 5-O-t-butyldimethylsilyl-4"-amino-4"deoxy-13-O-[2-(4'-O-oleandrosyl)-oleandrosyloxyethyl]-22,23-dihydro-13-epi-avermectin B₁ aglycone (mixture of isomers at C-4") which is identified by ¹H NMR and mass spectrometry.

EXAMPLE 49

5-O-t-butyldimethylsilyl-4"-amino-4"dexoy-13-O-[2-(4'-O-oleandrosyl)-oleandrosyloxyethyl]-avermectin B₁ aglycone Substitution of 5-O-t-butyldimethylsilyl-13-O-[2-(4'-O-oleandrosyl)-oleandrosyloxyethyl]-avermectin B₁ aglycone (Example 47) for 5-O-t-butyldimethylsilyl-13-O-[2-(4'-O-oleandrosyl)-oleandrosyloxyethyl]-22,23-dihydro-13-epi-avermectin B₁ aglycone in the procedure of Example 48 affords 5-O-t-butyldimethylsilyl-4"-amino-4"deoxy-13-O-[2-(4'-O-oleandrosyl)-oleandrosyloxyethyl]-avermectin B₁ aglycone (mixture of isomers at postition 4") which is identified by ¹H NMR and mass spectrometry.

EXAMPLE 50

5-O-t-butyldimethylsilyl-4"-methylamino-4"deoxy-13-O-[2-(4'-O-oleandrosyl)-oleandrosyloxyethyl]-22,23-dihydro-13-epi-avermectin B₁ aglycone Substitution of methylamine hydrochloride for ammonium acetate in the procedure of Example 48 affords 5-O-t-butyldimethylsilyl-4"-methylamino-4"-deoxy-13-O-[2-(4'-O-oleandrosyl)-oleandrosyloxyethyl]-22,23-dihydro-13-epi-avermectin B₁ aglycone (mixture of isomers at postition 4") which is identified by ¹H NMR and mass spectrometry.

EXAMPLE 51

4"-amino-4"-deoxy-13-O-[2-(4'-O-oleandrosyl)-oleandrosyloxyethyl]-22,23-dihydro-13-epi-avermectin B₁ aglycone Substitution of 5-O-t-butyldimethylsilyl-4"-amino-5-O-t-butyldimethylsilyl-4"-amino-4"deoxy-13-O-[2-(4'-O-oleandrosyl)-oleandrosyloxyethyl]-22,23-dihydro- 13-epi-avermectin B₁ aglycone (Example 48) for 4",5-bis-O-t-butyldimethylsilyl-13-O-[2-(4'-O-oleandrosyl)-oleandrosyloxyethoxymethyl]-22,23-dihydro-avermectin B₁ aglycone in the deprotection procedure of Example 36 affords 4"-amino-4"deoxy-13-O-[2-(4'-O-oleandrosyl)-oleandrosyloxyethyl]-22,23-dihydro-13-epi-avermectin B₁ aglycone (mixture of isomers at C-4") which is identified by ¹H NMR and mass spectrometry.

EXAMPLE 52

4"-amino-4"-deoxy-13-O-[2-(4'-O-oleandrosyl)-oleandrosyloxyethyl]-avermectin B₁ aglycone Substitution of 5-O-t-butyldimethylsilyl-4"-amino-5-O-t-butyldimethylsilyl-4"-amino-4"deoxy-13-O-[2-(4'-O-oleandrosyl)-oleandrosyloxyethyl]-avermectin B₁ aglycone (Example 49) for 4",5-bis-O-t-butyldimethylsilyl-13-O-[2-(4'-O-oleandrosyl)-oleandrosyloxyethoxymethyl]-22,23-dihydro-avermectin B₁ aglycone in the deprotection procedure of Example 36 affords 4"-amino-4"deoxy-13-O-[2-(4'-O-oleandrosyl)-oleandrosyloxyethyl]-avermectin B₁ aglycone (mixture of isomers at C-4") which is identified by ¹H NMR and mass spectrometry.

EXAMPLE 53

4"-methylamino-4"-deoxy-13-O-[2-(4'-O-oleandrosyl)-oleandrosyloxyethyl]-22,23-dihydro-13-epi-avermectin B₁ aglycone Substitution of 5-O-t-butyldimethylsilyl-4"-methylamino-5-O-t-butyldimethylsilyl-4"-amino-4"deoxy-13-O-[2-(4'-O-oleandrosyl)-oleandrosyloxyethyl]-22,23-dihydro-13-epi-avermectin B₁ aglycone (Example 50) for 4",5-bis-O-t-butyldimethylsilyl-13-O-[2-(4'-O-oleandrosyl)-oleandrosyloxyethoxymethyl]-22,23-dihydro-avermectin B₁ aglycone in the deprotection procedure of Example 36 affords 4"-methylamino-4"-deoxy-13-O-[2-(4'-O-oleandrosyl)-oleandrosyloxyethyl]-22,23-dihydro-13-epi-avermectin B₁ aglycone (mixture of isomers at C-4") which is identified by ¹H NMR and mass spectrometry.

EXAMPLE 54

4"-Acetylamino-4"-deoxy-13-O-[2-(4'-O-oleandrosyl)-oleandrosyloxyethyl]-22,23-dihydro-13-epi-avermectin B₁ aglycone Acetyl chloride (0.008 ml) is added to a cold (0° C.) solution of 4"-amino-4"deoxy-13-O-[2-(4'-O-oleandrosyl)-oleandrosyloxyethyl]-22,23-dihydro-13-epi-avermectin B₁ aglycone (Example 51, mixture of isomers at C-4") (100 mg) and triethylamine (0.031 ml) in 3 ml of dichloromethane. The solution is stirred at 0° C. for 1 hour then water (3 ml) is added. The layers are separated and the aqueous layer is extracted with dichloromethane (2×3 ml). The combined extracts are dried with MgSO₄, filtered and evaporated under vacuum. The crude product is purified by preparative layer silica gel chromatography to afford 4"-acetylamino-4"-deoxy-13-O-[2-(4'-O-oleandrosyl)-oleandrosyloxyethyl]-22,23-dihydro-13-epi-avermectin B₁ aglycone, which is identified by ¹H NMR and mass spectrometry.

EXAMPLE 55

4"-Acetylamino-4"-deoxy-13-O-[2-(4'-O-oleandrosyl)-oleandrosyloxyethyl]-avermectin B₁ aglycone Substitution of 4"-amino-4"deoxy-13-O-[2-(4'-O-oleandrosyl)-oleandrosyloxyethyl]-avermectin B₁ aglycone (Example 52, mixture of isomers at C-4") for 4"-amino-4"deoxy-13-O-[2-(4'-O-oleandrosyl)-oleandrosyloxyethyl]-22,23-dihydro-13-epi-avermectin B₁ aglycone in the procedure of Example 54 affords 4"-acetylamino-4"-deoxy-13-O-[2-(4'-O-oleandrosyl)-oleandrosyloxyethyl]-avermectin B₁ aglycone, which is identified by ¹H NMR and mass spectrometry.

What is claimed is:

1. A compound having the formula:

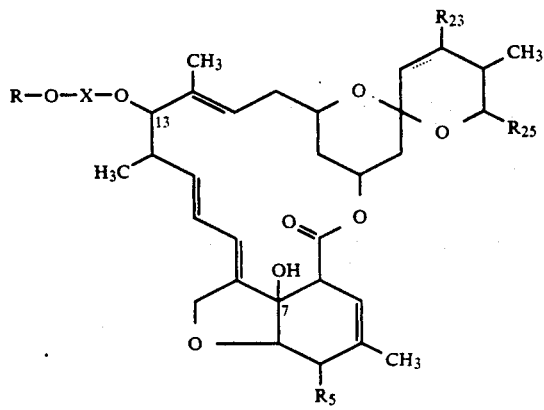

wherein:

R is a mono- or di-oleandrose, rhamnose, olivose, digitoxose, mycarose, daunosamine, glucose, ribose, galactose or 2-deoxy-ribose;

$X = -(CH_2)_n-$, $-CH_2CH_2OCH_2-$;

$n = 2-5$;

$R_5 = OH$, oxime;

$R_{23} = H$, OH, oxo (OH or oxo only if the broken line is a single bond);

$R_{25} = $ lower alkyl, lower alkenyl;

and the broken line indicates a single or double bond between carbons 22 and 23.

2. A compound having the formula:

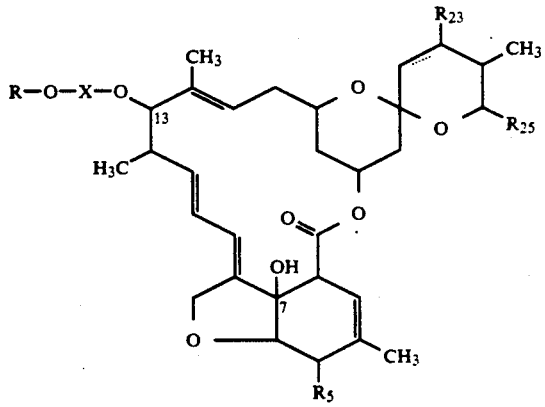

wherein
R is

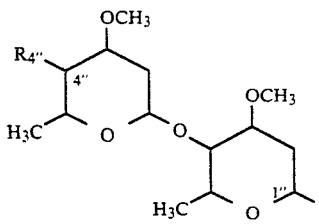

$R_{4''}$ is OH, NH$_2$, NH(loweralkyl), N(loweralkyl)$_2$ or NH(loweralkanoyl);

X = —(CH$_2$)$_n$—, —CH$_2$CH$_2$OCH$_2$—;

n = 2–5;

R$_5$ = OH, oxime;

R$_{23}$ = H, OH, oxo (OH or oxo only if the broken line is a single bond);

R$_{25}$ = lower alkyl, lower alkenyl;

and the broken line indicates a single or double bond between carbons 22 and 23.

3. The compound of claim 2 wherein

X = —(CH$_2$)$_n$—, —CH$_2$CH$_2$OCH$_2$—;

n = 2–5;

R$_5$ = OH;

R$_{4''}$ = OH, NH$_2$, NH(lower alkyl), NH(lower alkanoyl);

R$_{23}$ = H, OH, oxo (OH or oxo only if the broken line is a single bond);

R$_{25}$ = lower alkyl;

and the broken line indicates a single or double bond between carbons 22 and 23.

4. The compound of claim 3 wherein

X = (CH$_2$)$_n$;

n = 2–5;

R$_5$ = OH;

R$_{4''}$ = OH, NH(lower alkanoyl);

R$_{23}$ = H, OH, (OH only if the broken line is a single bond);

R$_{25}$ = isopropyl or sec-butyl;

and the broken line indicates a single or double bond between carbons 22 and 23.

5. The compound of claim 4 wherein

X = (CH$_2$)$_n$;

n = 2 or 3;

R$_5$ = OH;

R$_{4''}$ = OH;

R$_{23}$ = H;

R$_{25}$ = isopropyl or sec-butyl;

and the broken line indicates a single or double bond between carbons 22 and 23.

6. The compound of claim 2 which is 13-O-[2-(4'-O-oleandrosyl)-oleandrosyloxyethyl]-avermectin B$_1$ aglycone.

7. The compound of claim 2 which is 13-O-[2-(4'-O-oleandrosyl)-oleandrosyloxyethyl]-avermectin B$_2$ aglycone.

8. The compound of claim 2 which is 13-O-[2-(4'-O-oleandrosyl)-oleandrosyloxyethyl]-22,23-dihydro-avermectin B$_1$ aglycone.

9. The compound of claim 2 which is 13-O-[2-(4'-O-oleandrosyl)-oleandrosyloxyethyl]-13-epi-avermectin B$_1$ aglycone.

10. The compound of claim 2 which is 13-O-[2-(4'-O-oleandrosyl)-oleandrosyloxyethyl]-13-epi-avermectin B$_2$ aglycone.

11. The compound of claim 2 which is 13-O-[2-(4'-O-oleandrosyl)-oleandrosyloxyethyl]-22,23-dihydro-13-epi-avermectin B$_1$ aglycone.

12. The compound of claim 2 which is 13-O-[2-(4'-O-oleandrosyl)-oleandrosyloxyethoxymethyl]-22,23-dihydro-avermectin B$_1$ aglycone.

13. The compound of claim 2 which is 13-O-[3-(4'-O-oleandrosyl)-oleandrosyloxypropyl]-avermectin B$_1$ aglycone.

14. The compound of claim 2 which is 13-O-[3-(4'-O-oleandrosyl)-oleandrosyloxypropyl]-22,23-dihydro-avermectin B$_1$ aglycone.

15. The compound of claim 2 which is 13-O-[2-(4'-O-oleandrosyl)-oleandrosyloxyethyl]-22,23-dihydro-13-epi-avermectin B$_1$ aglycone-5-oxime.

16. The compound of claim 2 which is 13-O-[2-(4'-O-(4''-amino-4''-deoxy-oleandrosyl))-oleandrosyloxyethyl]-22,23-dihydro-13-epi-avermectin B$_1$ aglycone.

17. The compound of claim 2 which is 13-O-[2-(4'-O-(4''-acetylamino-4''-deoxy-oleandrosyl))-oleandrosyloxyethyl]-22,23-dihydro-13-epi-avermectin B$_1$ aglycone.

18. The compound of claim 2 which is 13-O-[2-(4'-O-(4''-acetylamino-4''-deoxy-oleandrosyl))-oleandrosyloxyethyl]-22,23-dihydro-avermectin B$_1$ aglycone.

19. The compound of claim 2 which is 13-O-[2-(4'-O-(4''-acetylamino-4''-deoxy-oleandrosyl))-oleandrosyloxyethyl]-avermectin B$_1$ aglycone.

20. The compound of claim 2 which is 13-O-[2-(4'-O-(4''-acetylamino-4''-deoxy-oleandrosyl))-oleandrosyloxyethyl]-13-epi-avermectin B$_1$ aglycone.

21. A method for the treatment of parasitic infections in animals which comprises treating such animals with an effective amount of a compound of claim 1.

22. A method for the treatment of pests of plants which comprises treating said plants or the soil in which they grow with an effective amount of a compound of claim 1.

23. A composition useful for the treatment of parasitic infections of animals or of pests of plants which is comprised of an inert carrier and an effective amount of a compound of claim 1.

* * * * *